(12) United States Patent
Tully et al.

(10) Patent No.: US 7,358,049 B2
(45) Date of Patent: *Apr. 15, 2008

(54) GENE CHIP TECHNOLOGY FOR DETERMINING MEMORY GENES

(75) Inventors: Timothy P. Tully, Cold Spring Harbor, NY (US); Joshua I. Dubnau, Huntington Station, NY (US); Michael Davis, Stone Mountain, GA (US); Jan Mous, Giebenach (CH); Ulrich Certa, Allschwil (CH)

(73) Assignees: Cold Spring Harbor Laboratory, Cold Spring Harbor, NY (US); Emory University, Atlanta, GA (US); Hoffmann-La Roche Inc., Nutley, NJ (US)

( * ) Notice: Subject to any disclaimer, the term of this patent is extended or adjusted under 35 U.S.C. 154(b) by 256 days.

This patent is subject to a terminal disclaimer.

(21) Appl. No.: 11/199,563

(22) Filed: Aug. 8, 2005

(65) Prior Publication Data

US 2006/0068422 A1    Mar. 30, 2006

Related U.S. Application Data

(63) Continuation of application No. 09/523,066, filed on Mar. 10, 2000, now Pat. No. 7,005,256.

(60) Provisional application No. 60/124,085, filed on Mar. 10, 1999.

(51) Int. Cl.
*C12Q 1/68* (2006.01)
*C12M 1/00* (2006.01)
*C07H 21/04* (2006.01)

(52) U.S. Cl. ............. 435/6; 435/91.1; 435/287.2; 536/23.1; 536/24.31

(58) Field of Classification Search ............... None
See application file for complete search history.

(56) References Cited

U.S. PATENT DOCUMENTS

| 5,143,854 A | 9/1992 | Pirrung et al. |
| 5,405,783 A | 4/1995 | Pirrung et al. |
| 5,445,934 A | 8/1995 | Fodor et al. |

(Continued)

FOREIGN PATENT DOCUMENTS

EP    0 834 576    4/1998

(Continued)

OTHER PUBLICATIONS

Dubnau, J. and Tully, T., "Gene Discovery in Drosophila: New Insights for Learning and Memory," *Annu. Rev. Neurosci.* 21:407-444 (1998).

(Continued)

*Primary Examiner*—B J Forman
(74) *Attorney, Agent, or Firm*—James A. Fox; Heller Ehrman LLP

(57) ABSTRACT

The present invention relates to methods of identifying genes involved in memory formation. This is accomplished by performing a gene chip identification of those genes expressed during transcription-dependent memory formation but not during transcription-independent memory formation. A statistical analysis of the gene chip identification output yields a set of genes that are involved in transcription-dependent memory formation.

26 Claims, 7 Drawing Sheets

U.S. PATENT DOCUMENTS

| | | | |
|---|---|---|---|
| 5,527,681 | A | 6/1996 | Holmes |
| 5,837,832 | A | 11/1998 | Chee et al. |
| 5,929,223 | A | 7/1999 | Tully et al. |
| 6,040,138 | A | 3/2000 | Lockhart et al. |
| 6,045,996 | A | 4/2000 | Cronin et al. |
| 6,051,559 | A | 4/2000 | Tully et al. |
| 7,005,256 | B1 * | 2/2006 | Tully et al. ............ 435/6 |

FOREIGN PATENT DOCUMENTS

| | | |
|---|---|---|
| WO | WO 90/15070 | 12/1990 |
| WO | WO 92/10092 | 6/1992 |
| WO | WO 92/10588 | 6/1992 |
| WO | WO 95/11995 | 5/1995 |
| WO | WO 96/11270 | 4/1996 |
| WO | WO 97/12976 | 4/1997 |
| WO | WO 98/49342 | 11/1998 |
| WO | WO 00/53810 | 9/2000 |

OTHER PUBLICATIONS

Yin, J.C.P., et al., "Induction of a Dominant Negative CREB Transgene Specifically Blocks Long-Term Memory in Drosophila," *Cell* 79:49-58 (1994).

Yin, J.C.P., et al., "CREB as a Memory Modulator: Induced Expression of a *dCREB2* Activator Isoform Enhances Long-Term Memory in Drosophila," *Cell* 81:107-115 (1995).

Josselyn, S.A., et al., "Overexpression of CREB in the Amygdala Facilitates the Formation of Long-Term Memory Measured with Fear Potentiated Startle in Rats," *Society for Neuroscience*, vol. 24, p. 926, Abstract 365.10 (1998).

Kogan, J.H., et al., "Spaced Training Induces Normal Long-Term Memory in CREB Mutant Mice," *Current Biology* 7:1-11 (1996).

Bartsch, D., et al., "Aplysia CREB2 Represses Long-Term Facilitation: Relief of Repression Converts Transient Facilitation into Long-Term Functional and Structural Change," *Cell* 83:979-992 (1995).

Bourtchouladze, R., et al., "Deficient Long-Term Memory in Mice with a Targeted Mutation of the cAMP-Responsive Element-Binding Protein," *Cell* 79:59-68 (1994).

Tully, T., et al., "Genetic Dissection of Consolidated Memory in Drosophila," *Cell* 79:35-47 (1994).

Ramsay, G., "DNA Chips: State-of-the art," *Nature Biotechnology* 16:40-44 (1998).

Silva, A.J., et al., "CREB and Memory," *Annu. Rev. Neurosci.* 21:127-148 (1998).

Guzowski, J.F., et al., "Antisense Oligodeoxynucleotide-Mediated Disruption of Hippocampal cAMP Response Element Binding Protein Levels Impairs Consolidation of Memory for Water Maze Training," *Proc. Natl. Acad. Sci.*, USA 94:2693-2698 (1997).

Tully, T., et al., "Independent Memories in Drosophila After Pavlovian Conditioning," *Society for Neuroscience Abstracts* 19(1/3):1066 Abstract 440.8(1993).

Cavallaro, S., et al., "Late Memory-Related Genes in the Hippocampus Revealed by RNA Fingerprinting," *Proc. Natl. Acad. Sci.*, USA 94:9669-9673 (1997).

Bourtchouladze, R., et al., "Different Training Procedures Recruit Either One or Two Critical Periods for Contextual Memory Consolidation, Each of Which Requires Protein Synthesis and PKA," *Learning & Memory* 5(4-5):365-374 (1998).

Pedreira, M.E., et al., "Massed and Spaced Training Build Up Different Components of Long-Term Habituation in the Crab *Chasmagnathus*," *Animal Learning & Behaviour* 26(1):34-45 (1998).

Luo, et al., "Hippocampal Gene Expression Analysis of Young and Aged Rats in Complex Maze Learning by cDNA Microarray," *Society of Neuroscience Abstracts* 25(1-2):2164 (1999).

Menzel, R., et al., "Massed and Spaced Learning in Honeybees: The Role of CS, US, the Intertrial Interval, and the Test Interval," *Learning & Memory* 8:198-208 (2001).

Bourtchouladze et al., "Different Training Procedures Recruit Either One or Two Critical Periods for Contextual Memory Consolidation, Each of Which Requires Protein Synthesis and PKA" Learning & Memory 5:365-374 (1998), XP001024521.

Cavallaro et al., "Late Memory-Related Genes in the Hippocampus Revealed by RNA Fingerprinting" Proc. Natl. Acad. Sci. USA, 94:9669-9673 (1997), XP002178412.

Guzowski et al., "Antisense Oligodeoxynucleotide-Mediated Distruption of Hippocampal cAMP Response Element Binding Protein Levels Impairs Consolidation of Memory for Water Maze Training" Proc. Natl. Acad. Sci. USA, 94;2639-2698 (1997), XP000934313 ISSN: 0027-8424.

Kogan et al., "Spaced Training Induces Normal Long-Term memory in CREB Mutant Mice" Current Biology, 7;1-11 (1996), XP001024551.

Pedreira et al., "Massed and Spaced Training Build Up Different Components of Long-Term Habituation in the Crab Chasmagnathus" Animal Learning & Behavior, 26(1);34-45 (1998), XP001024597.

Silva et al., "Creb and Memory" Annu. Rev. Neurosci, 21;127-148 (1998), XP000900517 ISSN:0147-006X.

Tully et al., "Independent Memories in Drosophila after Pavovian Conditioning" 19;1/3, pp. 1066 (Abstract) XP000566270 ISSN: 0190-5292, no date provided.

\* cited by examiner

Calculation of gene-expression level with Affy chips: 20 primer pairs per gene Average difference between PM and MM signal

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
agactaccga tgcgaacaac                                                  20

```
<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
gtccctgaac tggtcgtcta                                              20
```

GENE CHIP TECHNOLOGY FOR DETERMINING MEMORY GENES

RELATED APPLICATION

This application is a continuation of U.S. application Ser. No. 09/523,066, filed Mar. 10, 2000, now U.S. Pat. No. 7,005,256, which claims the benefit of U.S. Provisional Application No. 60/124,085, filed Mar. 10, 1999. The entire teachings of the above applications are incorporated herein in entirety by reference.

GOVERNMENT SUPPORT

The invention was supported, in whole or in part, by the following grants from the National Institutes of Health: Grant Nos. F32 HD08087-02, P01 HD33098-03, 7R37 MH-47840-09 and 5K05MH-00004-26. The United States Government has certain rights in the invention.

BACKGROUND OF THE INVENTION

An attribute that many organisms, including humans, possess is memory of past events. This attribute has been studied for many decades with much information now available that explains many of its ramifications. For example, two basic types of memory have been identified: transcription-independent memory, which includes short term memory, and transcription-dependent memory, which includes long term memory.

An heretofore relatively unknown aspect of memory is the identity of genes that contribute to its manifestation. The identity of the genes that contribute to memory formation is just beginning to be explored. Identification of genes associated with memory formation would provide (a) a genetic epidemiology of cognitive dysfunction, (b) diagnostic tools for individuals carrying different allelic forms of these genes (associative with different performance levels for particular forms of cognition) and (c) new targets for drug discovery ultimately to ameliorate various forms of cognitive dysfunction (and particular drugs could be matched to particular forms of cognitive dysfunction by the diagnostic tests). Thus, it would be useful to have techniques available that would identify the genes that are associated with memory formation.

SUMMARY OF THE INVENTION

The present invention is related to Applicants' discovery that the differential effects on memory formation produced by certain experimental protocols can be used to identify genes involved in transcription-dependent memory formation, particularly long term memory formation. The significant difference between any two experimental protocols is in the induction of transcription-dependent memory. The significant difference between any particular two experimental protocols to be compared is the induction of transcription-dependent memory in the experimental group and the absence of transcription-dependent memory in the control group.

Transcription-independent memory includes various "memory phases", such as short-term memory, intermediate-(or middle-) term memory and (in flies) anesthesia-resistant memory. In common to these forms is that pharmacological inhibitors of RNA transcription do not disrupt these memories. Transcription-dependent memory usually is referred to as long-term memory and inhibitors of RNA synthesis block its appearance.

As a result, Applicants' invention relates to methods of identifying a gene or genes involved in transcription-dependent memory (particularly long term memory) comprising (a) training non-human animals (particularly non-human mammals, other vertebrates and invertebrates) under conditions sufficient to induce transcription-dependent memory formation in the animals; (b) extracting RNA from brain tissue of the animals trained in step (a); (c) synthesizing DNA probes using the RNA extracted in step (b); (d) exposing the DNA probes synthesized in step (c) to microarray chips containing DNA sequences from genes of the genome of the animals under conditions appropriate for hybridization of the DNA probes to complementary DNA sequences on the microarray chips, wherein a signal is produced upon hybridization of the probes to complementary DNA sequences; (e) detecting the signal produced in step (d); and (f) performing a statistical comparison between the signal detected in step (e) and the signal detected in a control.

In one embodiment, the control is obtained according to a method comprising (i) training non-human control animals under appropriate conditions, wherein the conditions are insufficient to induce transcription-dependent memory formation in the control animals; (ii) extracting RNA from brain tissue of the control animals trained in step (i); (iii) synthesizing DNA probes using the RNA extracted in step (ii); and (iv) exposing the DNA probes synthesized in step (iii) to microarray chips containing DNA sequences from genes of the genome of the animals under conditions appropriate for hybridization of the DNA probes to complementary DNA sequences on the microarray chips, wherein a signal is produced upon hybridization of the probes to complementary DNA sequences. The experimental conditions of step (a) and step (i) constitute an (experimental) treatment pair. The significant difference between the experimental conditions of step (a) and step (i) is in the induction of transcription-dependent memory.

In a second embodiment, the control is obtained according to a method comprising (i) extracting RNA from brain tissue of non-human control animals; (ii) synthesizing DNA probes using the RNA extracted in step (i); and (iii) exposing the DNA probes synthesized in step (ii) to microarray chips containing DNA sequences from genes of the genome of the animals under conditions appropriate for hybridization of the DNA probes to complementary DNA sequences on the microarray chips, wherein a signal is produced upon hybridization of the probes to complementary DNA sequences. In this embodiment of the control, the control animals are naïve (untrained) animals.

As used herein, a control animal is an animal that is of the same species as, and otherwise comparable to (e.g., similar age, sex), the animal that is trained under conditions sufficient to induce transcription-dependent memory formation in that animal.

In a particular embodiment, RNA is extracted from the amygdala of trained or control animals. In another embodiment, RNA is extracted from the hippocampus of trained or control animals. In still another embodiment, the signal from hybridized probes is amplified prior to detection. In another embodiment, a statistical comparison is made (performed, conducted) between the signal detected in step (e) and the signal detected in a control that is obtained by training control animals under conditions sufficient to induce transcription-independent memory but not transcription-dependent long term memory.

Transcription-dependent memory can be induced using specific experimental conditions. In one embodiment, transcription-dependent memory is induced in a non-human animal using a spaced training protocol for the fear-potentiated startle response. In a second embodiment, transcription-dependent memory is induced in a non-human animal using a shuttle-box avoidance protocol. In a third embodiment, transcription-dependent memory is induced in a non-human animal using a contextual fear conditioning protocol.

The invention also relates to a method of identifying a gene or genes involved in transcription-dependent memory in *Drosophila* comprising (a) training *Drosophila* under conditions appropriate to induce transcription-dependent memory formation in the *Drosophila*; (b) extracting RNA from head tissue of *Drosophila* trained in step (a); (c) synthesizing DNA probes using the RNA extracted in step (b); (d) exposing the DNA probes synthesized in step (c) to microarray chips containing DNA sequences from genes of the *Drosophila* genome under conditions appropriate for hybridization of the DNA probes to complementary DNA sequences on the microarray chips, wherein a signal is produced upon hybridization of the probes to complementary DNA sequences; (e) detecting the signal produced in step (d); and (f) performing a statistical comparison between the signal detected in step (e) and the signal detected in a control.

In a particular embodiment, the control is obtained according to a method comprising (i) training control *Drosophila* under appropriate conditions, wherein the conditions are insufficient to induce transcription-dependent memory formation in the control *Drosophila*; (ii) extracting RNA from head tissue of the control *Drosophila* trained in step (i); (iii) synthesizing DNA probes using the RNA extracted in step (ii); and (iv) exposing the DNA probes synthesized in step (iii) to microarray chips containing DNA sequences from genes of the *Drosophila* genome under conditions appropriate for hybridization of the DNA probes to complementary DNA sequences on the microarray chips, wherein a signal is produced upon hybridization of the probes to complementary DNA sequences. The experimental conditions of step (a) and step (i) constitute an (experimental) treatment pair. The significant difference between the experimental conditions of step (a) and step (i) is in the induction of transcription-dependent memory.

In a second embodiment, the control is obtained according to a method comprising (i) extracting RNA from head tissue of control *Drosophila*; (ii) synthesizing DNA probes using the RNA extracted in step (i); and (iii) exposing the DNA probes synthesized in step (ii) to microarray chips containing DNA sequences from genes of the *Drosophila* genome under conditions appropriate for hybridization of the DNA probes to complementary DNA sequences on the microarray chips, wherein a signal is produced upon hybridization of the probes to complementary DNA sequences. In this embodiment of the control, control *Drosophila* are naïve (untrained) flies.

As used herein, a control *Drosophila* is a *Drosophila* that is of the same species as, and otherwise comparable to, the *Drosophila* that is trained under conditions sufficient to induce transcription-dependent memory in that *Drosophila*.

In one embodiment of the method of identifying a gene or genes involved in transcription-dependent memory in *Drosophila*, the DNA probes are labeled with a fluorescent marker and the signal is detected using a fluorescence assay. In a particular embodiment, the signal from hybridized probes is amplified prior to detection. In another embodiment, a statistical comparison is performed between the signal detected in step (e) and the signal detected in a control that is obtained by training control *Drosophila* under conditions sufficient to induce transcription-independent memory but not transcription-dependent memory.

Transcription-dependent memory can be induced in *Drosophila* using a spaced training protocol (e.g., spaced training of olfactory Pavlovian conditioning). Transcription-independent memory can be induced in *Drosophila* using a massed training protocol (massed training of olfactory Pavlovian conditioning).

A statistically significant difference in transcript level for a specific gene between animals trained under conditions sufficient to induce transcription-dependent memory and control animals trained under appropriate conditions that are not sufficient to induce transcription-dependent memory identifies that gene as a candidate memory gene (CMG). In a particular embodiment, a statistically significant difference in transcript level between spaced- and massed-trained groups for a specific gene identifies that gene as a candidate memory gene.

A statistically significant difference in transcript level for a specific gene between animals trained under conditions sufficient to induce transcription-dependent memory and naïve (untrained) control animals identifies that gene as a candidate plasticity gene (CPG). In a particular embodiment, a statistically significant difference in transcript level between spaced-trained and untrained groups for a specific gene identifies that gene as a candidate plasticity gene.

DETAILED DESCRIPTION OF THE INVENTION

Figure 1:
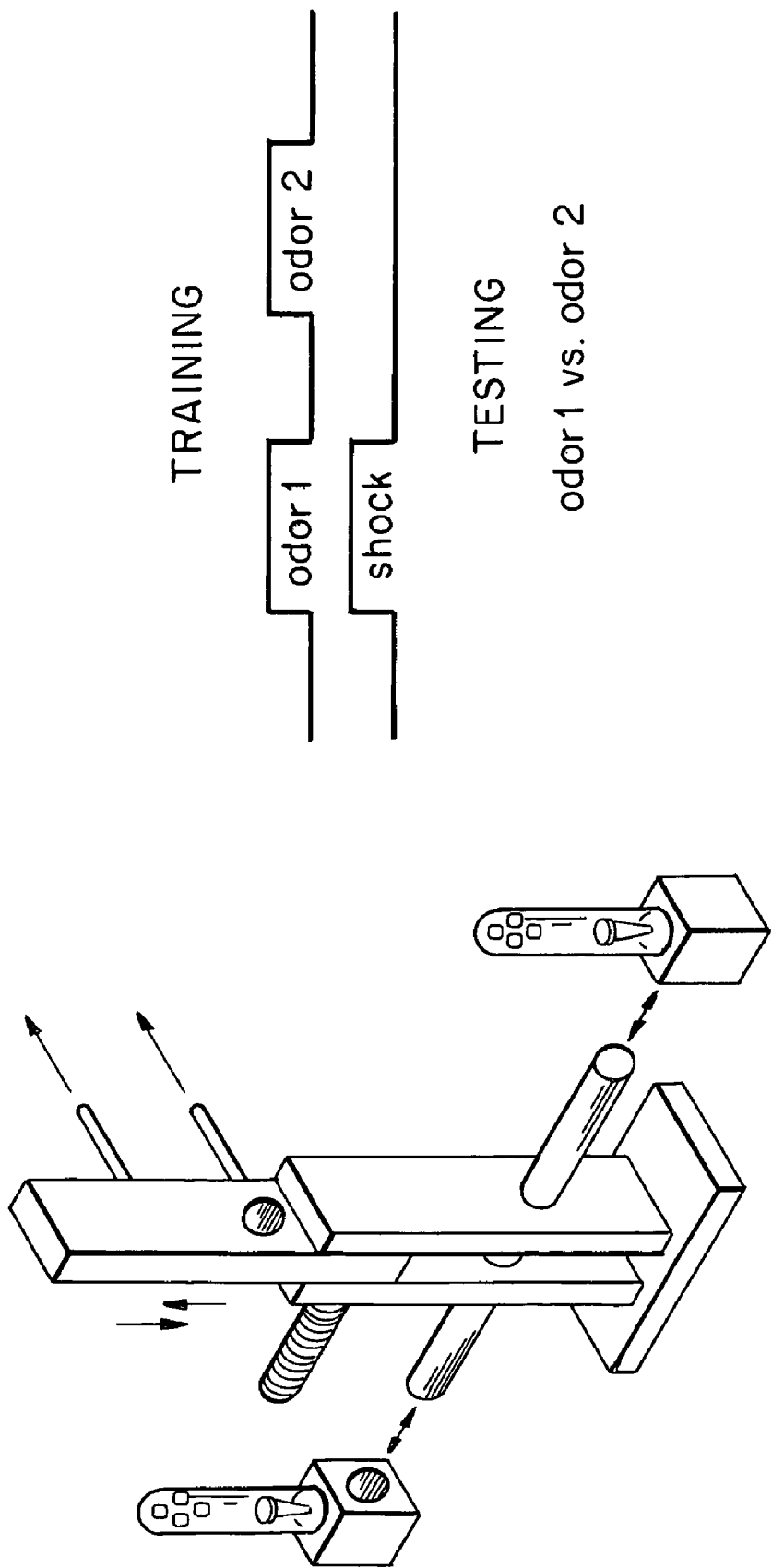
FIG. 1 is a schematic diagram of a training protocol described in Tully et al., *Cell,* 79:35-47 (1994)), which produces Pavlovian olfactory learning in flies.

To produce a specific "long-term memory," an animal is subjected to a specific training protocol under controlled, experimental conditions. In Pavlovian conditioning procedures, for instance, two specific stimuli are presented in temporal contiguity to produce "associative learning and memory." One of the two stimuli is designated a "conditioned stimulus" (CS) and the other is designated an "unconditioned stimulus" (US). The US usually is a natural reinforcer that elicits a "unconditioned response" (UR) before training in a "reflexive" manner. With CS-US pairing, a "conditioned response" (CR) begins to appear in response to the CS before (or in the absence of) presentation of the US. After a CR to a specific CS-US pairing is "learned", memory formation thereafter begins.

Memory formation of this specific, experimental experience can exist in two general forms: a transcription-independent form and a transcription-dependent form. The former includes various "memory phases," such as short-term memory, intermediate-(or middle-) term memory and (in flies) anesthesia-resistant memory. In common to these forms is that pharmacological inhibitors of RNA transcription do not disrupt these memories. The latter form usually is referred to as long-term memory and inhibitors of RNA synthesis block its appearance.

In animal models, various experimental treatments, such as gene mutation, pharmacological blockade, anatomical lesion or specific training protocols, can affect one or more of these types of memories. In particular, some experimental treatments yield normal amounts of transcription-independent memory but do not yield transcription-dependent memory. Such observations constitute the basis of informative DNA chip comparisons. In general, a comparison is made between two experimental protocols; one (experimental group) that is sufficient to induce both transcription-independent and transcription-dependent memories and one that yields only transcription-independent memory (control group). Any detectable differences in transcript levels between these two protocols then can be attributed specifically to a transcription-dependent memory of the experimentally induced learning. These transcripts are referred to herein as "Candidate Memory Genes" (CMGs).

Although experimental conditions are controlled to induce a specific type of learning, other experimentally uncontrolled forms of learning also may take place. Thus, although a control group may not yield transcription-dependent memory of the specific experimental task, it nevertheless may yield a transcription-dependent memory of an uncontrolled learning experience. One type of such experience is the potential "nonassociative" forms of learning that occur in response to only the CS or US (alone), or in response to CS-US presentations that are not paired temporally (which is the key requirement for "associative learning"). Hence, transcription-dependent "nonspecific" memories may exist in control groups, as defined above. This observation gives rise to a broader class of transcripts involved with "nonspecific" learning, which we refer to as Candidate Plasticity Genes (CPGs). DNA chip comparisons between an experimental group, as defined above, and naîîve (untrained) animals will yield CPGs, along with CMGs.

Figure 2:
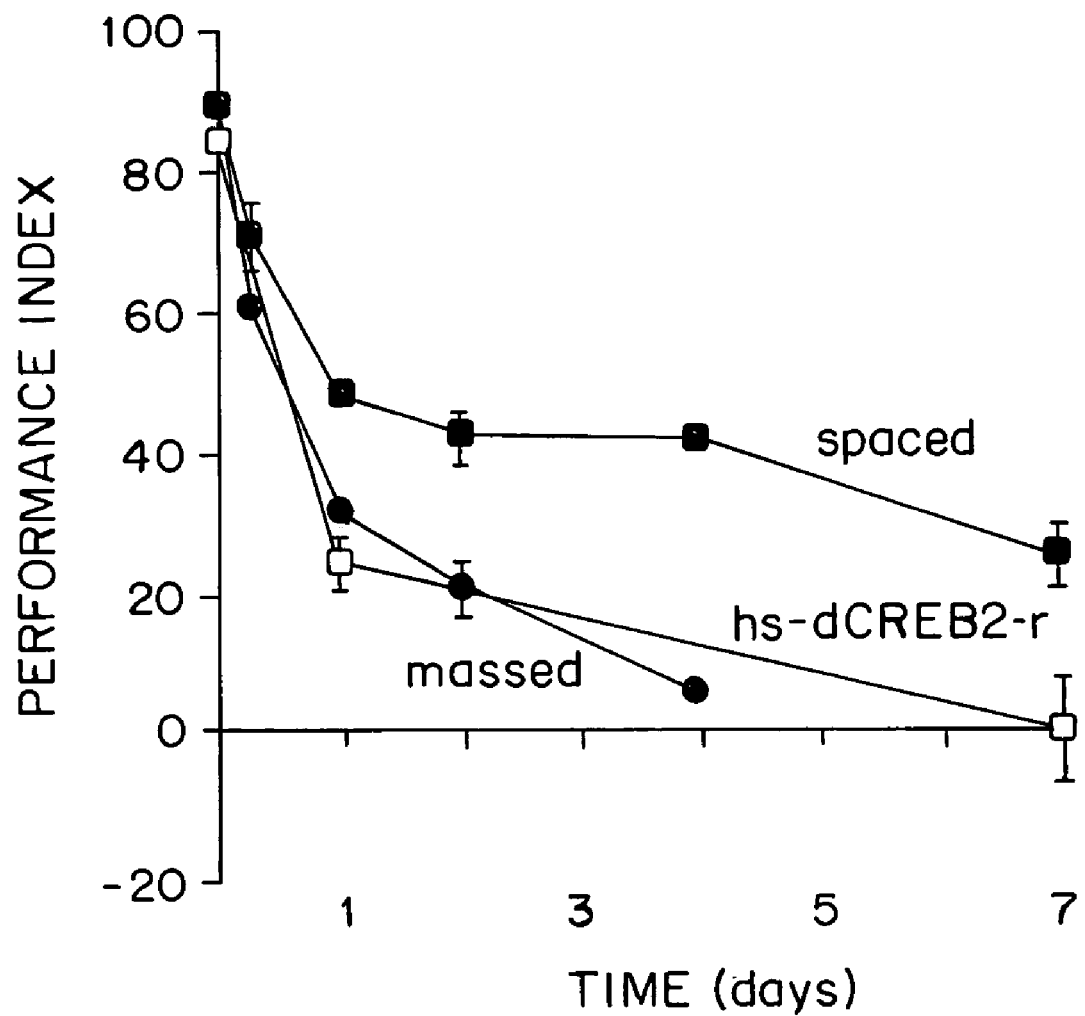
FIG. 2 is a graphic representation of results showing memory retention after spaced or massed training in normal (wild type) flies or spaced training in transgenic hs-CREB2-r flies after induced expression of CREB repressor (see Yin et al., *Cell,* 79:49-58 (1994)). Learning and early memory (cycloheximide insensitive) are normal in transgenic flies. The additional (protein synthesis-dependent LTM) memory normally produced by spaced training is blocked in transgenic flies. This comparison reveals that the only difference between spaced and massed training is the appearance of a transcription-dependent memory after the former.
Figure 3:
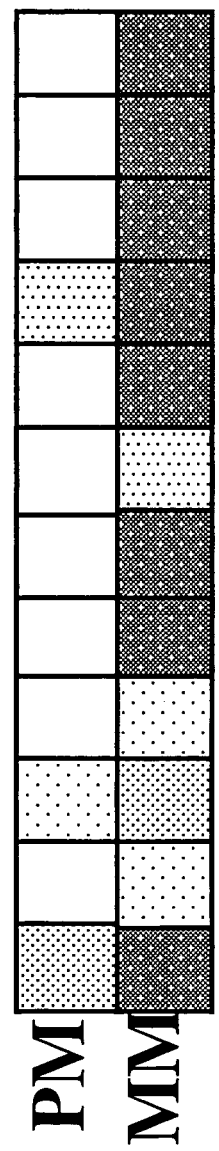
FIG. 3 is a schematic diagram showing the average difference between signal detected for a specific DNA oligonucleotide probe perfectly matched (PM) (complementary) to a specific section of a specific gene and signal detected for that probe mismatched (MM) to that section of the gene as a result of the introduction of a nucleotide sequence error (mutation) in that section of the gene. The average difference between PM and MM pairs, and usually for 20 pairs per gene, is determined by Affymetrix design software analysis (Affymetrix, Inc., Santa Clara, Calif.). The squares represent microsequences on a microarray chip.
Figure 4A:
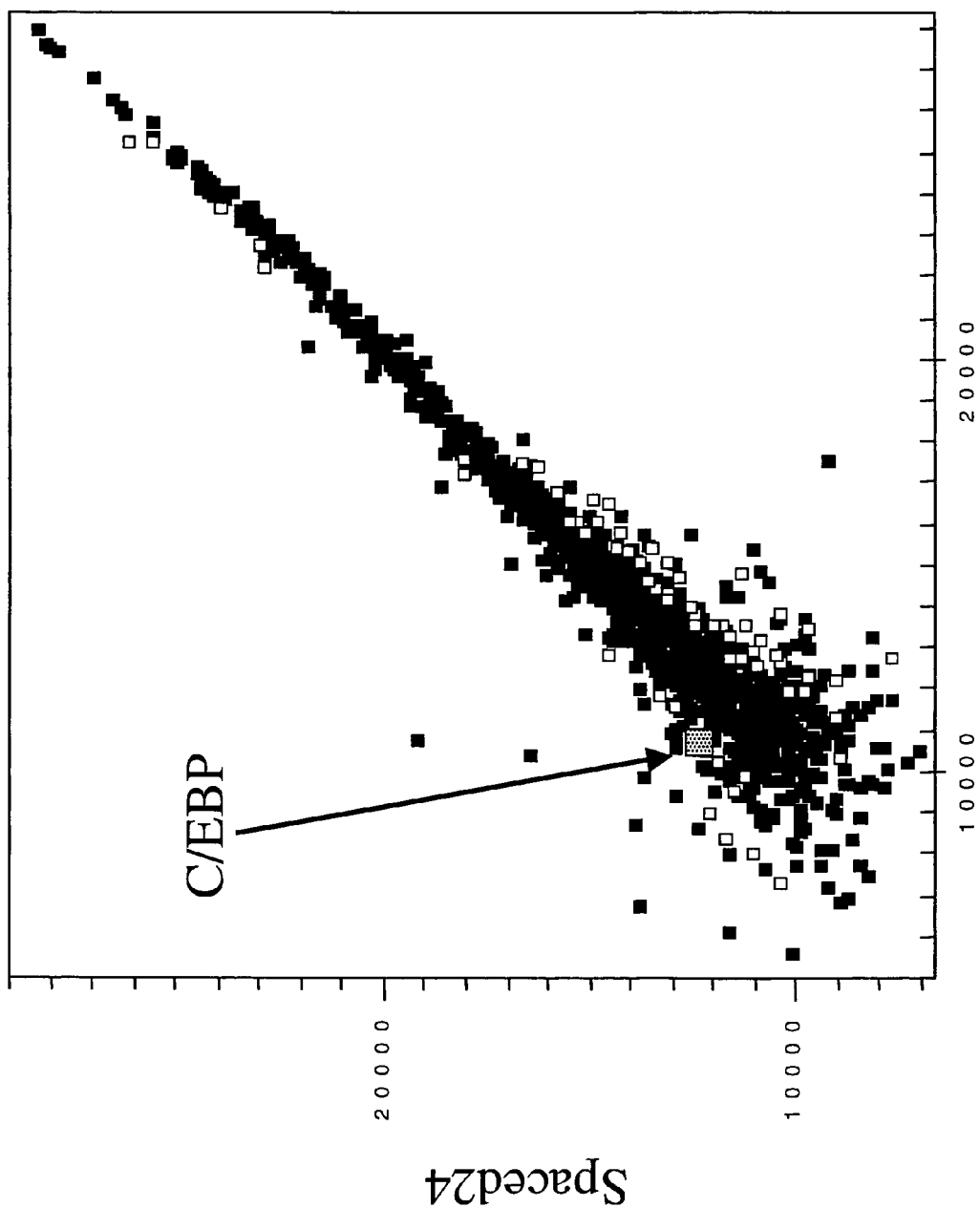
FIG. 4A is a scatterplot representation (spaced versus massed) of the mean signal (mean transformed normalized difference) from an N=10 chips, for each cloned *Drosophila* gene, each hybridized with DNA probes made from RNA extracted from the heads of normal *Drosophila* exposed 24 hours earlier to either spaced or massed training. Each square represents a specific *Drosophila* gene, 1542 of which are contained on each chip. The candidate memory genes are identified by the lighter shaded squares. The location of the C/EBP gene in the plot is indicated in the figure.
Figure 4B:
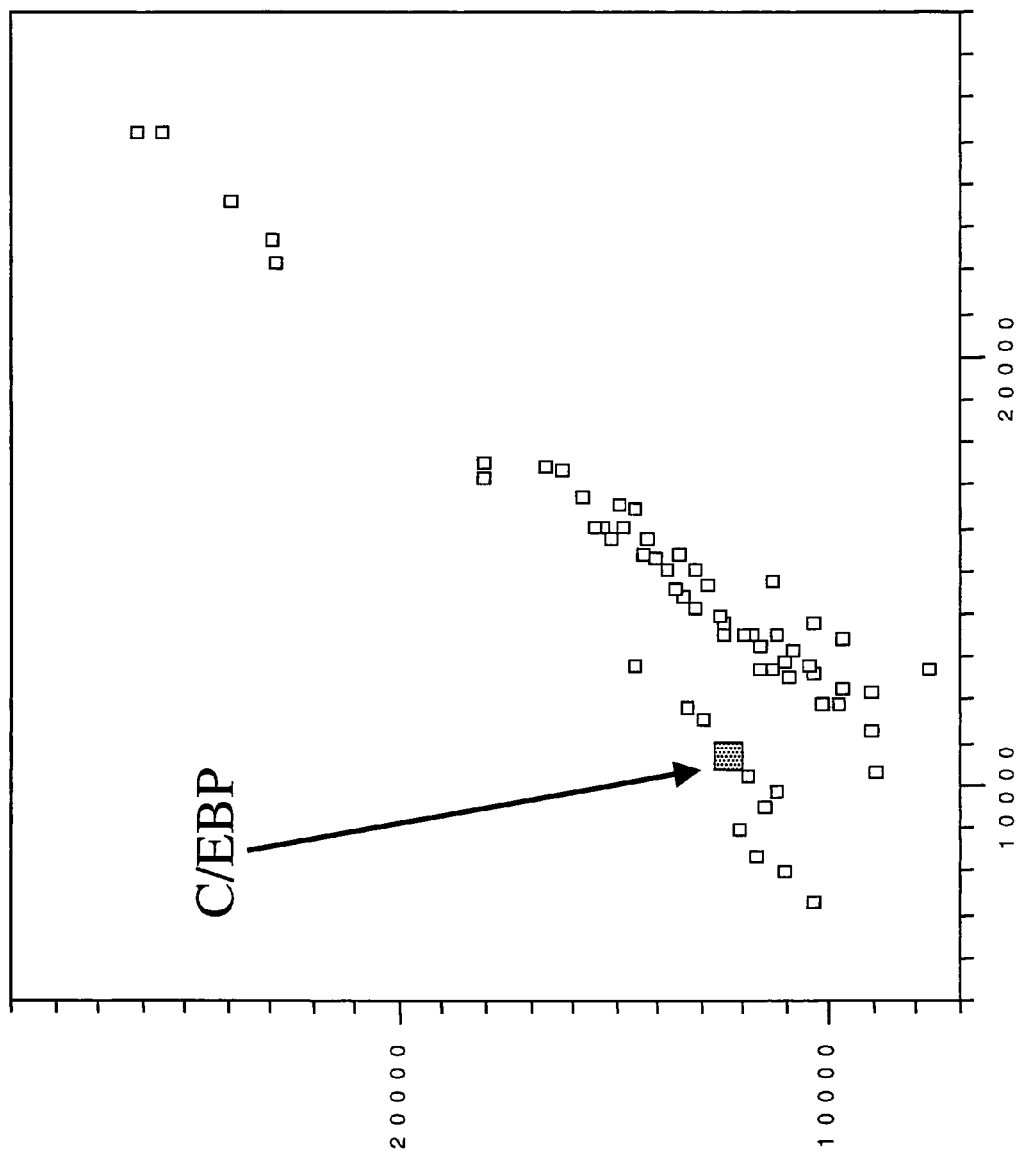
FIG. 4B is a scatterplot representation (spaced verus massed) showing the statistically significant values from FIG. 4A. Each square represents a specific *Drosophila* gene, 1542 of which are contained on each chip. The location of the C/EBP gene in the plot is indicated in the figure.

Behavior-genetic studies in *Drosophila* have established a pair of training protocols with differential effects on memory formation after a Pavlovian odor-shock learning paradigm. Ten training sessions "massed" together (i.e., with no rest interval between sessions) yields maximal learning (acquisition) and transcription-independent memories (not protein synthesis-dependent) (early memories, short-term memory). In contrast, ten training sessions "spaced" (i.e., with a 15-minute rest interval between sessions) yields equivalent levels of learning and transcription-independent memories (early memories), as well as maximal levels of transcription-dependent memory (including protein synthesis-dependent long-term memory (LTM)). LTM requires spaced training; even 48 massed training sessions fails to induce LTM (Tully et al., *Cell*, 79:35-47 (1994)). Protein synthesis-dependent LTM induced by spaced training is blocked completely via overexpression of CREB repressor (FIG. 1) (Yin et al., *Cell*, 79:49-58 (1994)). The resulting memory curve after spaced training, where protein synthesis- and CREB-dependent LTM is blocked, is similar to that produced by massed training in normal flies. In contrast, overexpression of CREB activator induces LTM with less training (one training session) or with massed training (FIG. 2) (Yin et al., *Cell*, 81:107-115 (1995)). Hence, the induction of LTM is both protein synthesis- and CREB-dependent. These results demonstrate that the only functional difference between spaced and massed training protocols is the appearance of transcription-dependent memory after the former.

This observation forms the basis of a differential screen to identify additional "downstream" genes that are transcriptionally regulated during transcription-dependent memory formation. DNA probes were synthesized using RNA extracted from the heads of spaced- or massed-trained flies according to methods generally known in the art (see, e.g., Sambrook et al., Eds., *Molecular Cloning: A Laboratory Manual*, 2nd edition, Cold Spring Harbor University Press, New York (1989); and Ausubel et al., Eds., *Current Protocols In Molecular Biology*, John Wiley & Sons, New York (1997)). RNA was extracted from fly heads as described previously (see, e.g., Drain et al., *Neuron*, 6:71-82 (1991), which is incorporated herein by reference). Spaced- and massed-training of flies were conducted as described previously (see, e.g., Tully et al., *Cell*, 79:35-47 (1994); and Tully and Quinn, *J. Comp. Physiol.*, 157:263-277 (1985), which are incorporated herein by reference). Complementary DNA (cDNA) probe was synthesized from the extracted RNA according to methods generally known in the art (see, e.g., Sambrook et al., Eds., *Molecular Cloning: A Laboratory*

Manual, 2nd edition, Cold Spring Harbor University Press, New York (1989); and Ausubel et al., Eds., Current Protocols In Molecular Biology, John Wiley & Sons, New York (1997)). The complex cDNA probe mixture then was hybridized onto microarray chips containing DNA sequences (target DNA sequences) of 1542 Drosophila genes (Affymetrix, Inc., Santa Clara, Calif.; see also, e.g., U.S. Pat. No. 5,445, 934; and Ramsay, Nature Biotechnology, 16:40-44 (1998), which are incorporated herein by reference). In a particular embodiment, the DNA probes are labeled with a detectable marker (e.g., fluorescent marker). The signal from hybridized DNA probes was amplified and detected according to methods generally known in the art (see, e.g., Sambrook et al., Eds., Molecular Cloning: A Laboratory Manual, 2nd edition, Cold Spring Harbor University Press, New York (1989); and Ausubel et al., Eds., Current Protocols In Molecular Biology, John Wiley & Sons, New York (1997)). In a particular embodiment, hybridization was detected using a fluorescence assay. A statistical comparison (DNA chip comparison) was made (performed) by comparing the signal detected between spaced- and massed-trained groups.

A sample size and signal transformation algorithm has been determined that improves the statistical reliability to detect small differences in transcript levels between spaced- and massed-trained groups. In a preferred embodiment, it has been determined that a sample size of 10 chips per treatment group for each treatment protocol (i.e., for each gene, 10 chips for spaced-trained group and 10 chips for massed-trained group) improves the statistical reliability to detect small differences in transcript levels between spaced- and massed-trained groups. In a preferred embodiment, statistical comparison (DNA chip comparison) is made using the following signal transformation algorithm:

1. Determine the "average difference" between signal detected for a set of primer pairs for specific gene. The average difference between perfect matched (PM) and mismatched (MM) signals is determined by Affymetrix design software analysis (Affymetrix, Inc., Santa Clara, Calif.).
2. Box-Cox Transformation:
   Any average difference value below 10 is eliminated. The remaining average difference values for each gene on each chip then are normalized by the overall average difference (across all genes) for that entire chip.

Grand Mean=Overall Avg. Diff. for all chips and all genes/chip $$\text{Normalization Factor (for Chip X)} = \frac{\text{Overall Avg. Diff. for Chip X}}{\text{Grand Mean}}$$

Norm(Avg. Diff.)=(Norm. Factor for Chip X)×(Gene Y on Chip X)

Transformed Avg. Diff.={ln [norm(Avg. Diff.)]}×2720.75

3. Determine the mean and standard error. Compare mean for spaced- and massed-trained flies for each Gene Y using standard t-tests (alpha=0.05). If $p \leq 0.05$, then the mean signal transformation for a given gene in spaced-trained flies is considered to be statistically different from the mean signal transformation for that gene in massed-trained flies.

Alternatively, statistical comparison (DNA chip comparison) can be made using the following signal transformation algorithm:

1. Determine the "average difference" between signal detected for a set of primer pairs for specific gene. The average difference between perfect matched (PM) and mismatched (MM) signals is determined by Affymetrix design software analysis (Affymetrix, Inc., Santa Clara, Calif.).
2. Box-Cox Transformation:
   Any negative average difference for a given gene is zeroed. The "average difference zeroed" (Avg. Diff. 0) for each gene on each chip is normalized by the overall "average difference" for that entire chip.

a) Avg. Diff. 0 = Avg. Diff., if Avg. Diff. ≥ 0,
   = 0, if Avg. Diff. < 0 b) Normalization:

Grand Mean=Overall Avg. Diff. for all chips and all genes/chip $$\text{Normalization Factor (for Chip X)} = \frac{\text{Overall Avg. Diff. for Chip X}}{\text{Grand Mean}}$$

Norm(Avg. Diff. 0)=Normalization Factor(for Chip X)×(Gene Y on Chip X)(for each gene)

(c) Transformed Avg. Diff.={ln [norm(Avg. Diff.0)]}×2720.75136

3. Determine the mean and standard error. Compare spaced mean versus massed mean with a t-test comparison. If $p \leq 0.05$, then the mean signal transformation for a given gene in spaced-trained flies is considered to be statistically different from the mean signal transformation for that gene in massed-trained flies.

Other signal transformation algorithms can be used in performing a statistical comparison (DNA chip comparison) of signal detected between spaced- and massed-trained groups.

With these proprietary approaches, 1542 statistical spaced versus massed training comparisons (Student t-tests) have been determined from Drosophila. Candidate memory genes (CMGs) (not including transposable elements or mitochondrial genes), which are transcriptionally regulated during transcription-dependent memory formation, were identified from the DNA chip comparisons (statistical comparisons) between spaced- and massed-trained groups. Transcripts that are differentially regulated represent those involved specifically in "associative" LTM induced by a Pavlovian odor-shock learning paradigm.

CMGs from Drosophila determined from statistical analysis using the signal transformation algorithm in which an average difference value below 10 for a given gene is deleted, from the spaced versus massed comparison (24-hour memory), are presented in Table 1. CMGs from Drosophila determined from statistical analysis using the signal transformation algorithm in which a negative average difference value for a given gene is zeroed, from the spaced versus massed comparison (24-hour memory), are presented in Table 2.

TABLE 1

Statistical Candidate Memory Genes, derived from statistical analysis (delete avg. diff. values <10), from the spaced versus massed comparison (24-hour memory).

hikaru genki type 1 product
inositol 1,4,5-trisphosphate receptor
mitochondrial cytochrome c oxidase subunits, ATPase6, 7 tRNAs
mitochondrial cytochrome c oxidase subunits, ATPase6, 7 tRNAs
mitochondrial cytochrome c oxidase subunits, ATPase6, 7 tRNAs
C/EBP gene
disabled
molybdenum cofactor (cin)
dif
syntaxin1A (syx-1A)
fsh membrane protein, 7.6 kb mRNA
defective chorion fc177 (dec-1) gene
mitochondrial DNA with 12 tRNAs and 7 genes.
proteasome (PROSA-28.1.1.)
cysteine-string protein 32 (csp32)
FTZ-F1 mRNA
Mov34 protein mRNA
transcription factor TFIID 230 kda subunitnt
croc/FD1 = crocodile
CS-5 pheromone-binding protein homolog OS-E mRNA
mago-nashi protein (mgn) gene
transcription initiation factor TFIID 28 kDa subunit mRNA
Canton S RNA binding protein La/SS-B (DLa/SS-B) mRNA
angiotensin converting enzyme precursor (Ance) mRNA
commissureless (comm) mRNA
nuclear hormone receptor superfamily member DHR78 (DHR78) mRNA
larval serum protein 1 beta subunit (Lsp-1b) gene
cut locus mRNA for homeodomain-containing protein
DRI class II gene for type I regulatory subunit of cAMP-dependent kinase PO gene
PP1 13C gene for protein phosphatase 1 13C
mRNA for 51 kDa protein
genes mst 355a and 355b for male accessory gland secretory protein
PP-Y mRNA for protein phosphatase Y (EC 3.1.3.)
anon-66Da, Minute(3)66D and anon-66Db genes
mRNA for 5HT-dro2A receptor (serotonin receptor).
eye color protein (garnet) mRNA
sparkling protein (spa) mRNA
kinesin-related protein (costal-2) mRNA
Fuzzy (fuzzy) mRNA
chitinase (CHT4) gene
mRNA for rab11
neu = neuralized mRNA
anachronism Genomic/mRNA
TART-B1 transposon putative single-stranded nucleic acid bind
sodium channel protein (para) gene, exons 9, 10, 11, 12
mod2.2 (mod(mdg4)) mRNA
tyrosine kinase mRNA
leucine-rich repeat/Ig transmembrane protein KEK1 precursor
gliolectin mRNA
Deformed epidermal autoregulatory factor-1 (Deaf1) mRNA
Lozenge (lz) mRNA
hook (hook) mRNA
SH2/SH3 adaptor protein (Dock) mRNA
retinoid- and fatty acid-binding glycoprotein mRNAblown fuse protein (blow) mRNA
GCR 101 mRNA
mRNA for metabotropic glutamate receptor
mRNA for ladybird late homeodomain transcription factor
mRNA for putative mitochondrial protein, partial
colt gene
mRNA for nuclear protein SA

TABLE 2

Statistical Candidate Memory Genes from Drosophila, derived from statistical analysis (negative avg. diff. value is zeroed), from the spaced versus massed comparison (24-hour memory).

hikaru genki type1 gene
tyrosine kinase hopscotch gene
syntaxin-1A (syx-1A) gene
proteasome (PROSA-28.1.1.) gene
P-glycoprotein (MdR 49) gene
Mov34 protein gene
POU domain protein (pdm-1) gene
Drosophilia melanogaster epidermal growth factor-like protein (spitz) gene
(clone 10B-1) germ cell-less protein (gc11) gene
mago-nashi protein (mgn) gene
serotonin transporter gene
transcription initiation factor TFIID 28 kDa subunit gene
ribonucleoside-diphosphate reductase large subunit gene
nudel (ndl) gene
bithorax complex (BX-C) gene cluster
commissureless (comm) gene
DNA polymerase gamma gene
larval serum protein 1 beta subunit (Lsp-1b) gene
hdl cuticle gene cluster
alpha-methyldopa hypersensitive gene 1(2)amd gene
Shaker ShB gene
DNA-binding protein E1f1 gene
chorion protein s16 gene
Adh and Adh-dup genes
E2F gene
51 kDa protein gene
caupolican homeoprotein gene
5HT-dro2A receptor gene
odorant binding protein LUSH (lush) gene
eye color protein (garnet) gene
adenylyl cyclase isoform DAC9 gene
kinesin-related protein (costal-2) gene
chitinase (CHT1) gene
canoe gene
rab11 gene
imitation-SWI protein (ISWI) gene
receptor guanylyl cyclase (DGC1) gene
tumor supressor (warts) gene
kinesin-like protein (KLP4) gene
myosin-IA gene
cytoplasmic basic protein (deltex) gene
Ca/calmodulin-dependent nitric oxide synthase (NOS) gene
sodium channel protein (para) gene
CKII alpha subunit interactor 1 (CKIIalpha-I1) gene
leucine-rich repeat/Ig transmembrane protein KEK1 precursor (kek1) gene
geranylgeranyl transferase beta-subunit type I (beta GGT-I) gene
hook (hook) gene
SH2/SH3 adaptor protein (Dock) gene
RNA-binding protein lark (lark) gene
retinoid-and fatty acid-binding glycoportein gene
Dreg-2 protein gene
transcription factor dMax gene
non-histone chromosomal protein Prod (prod) gene
blown fuse protein (blow) gene
orb gene
angel gene
ladybird late homeodomain transcription factor gene The statistical procedures described above only suggest "statistical candidates." A fundamental aspect of the statistical methods employed (as well as other such methods) is that "false positive" and "false negative" candidates are obtained along with the "true positives." Hence, an independent method of detecting experience-dependent changes in gene transcription must be applied to the "statistical candidates." Such independent methods include Northern blot analysis, quantitative polymerase chain reaction (QPCR) and RNase protection assays, and can be used to confirm the statistical candidates identified. The quantitative analyses of these data also are subject to false positive and false negative results.

Minor changes in the statistical methods herein can yield a different set of "statistical candidates". Often times, more than one type of data transformation is sufficient to yield a normalized distribution of difference scores. Each data transformation used, however, will yield a different set of statistical candidates. All methods of signal detection also must resolve "baseline values", which are too low for accurate detection. Setting such values to "zero" is one way to deal with this difficulty. Another way is to eliminate such values from the data set (e.g., eliminate values of less than 10, for example).

Chip data provide confirmatory information, gene-by-gene, as to which transcripts are involved with memory. Chip data also provide exact coordinated transcriptional response to different stimuli across all gene transcripts. In particular, chip data provide information as to the coordinated effect a gene transcript has on memory.

Most genes in Drosophila have been shown to have mammalian homologs, and such is the case for most Drosophila genes involved in memory formation (Dubnau and Tully, Ann. Rev. Neurosci., 21:407-444 (1998)). With the growing knowledge that mammalian homologs can be functionally substituted in Drosophila for its fly homolog, the present discovery directly implicates the corresponding mammalian homologs.

The differential effects on long-lasting memory produced by spaced versus massed training is a phenomenon widely observed in the animal kingdom. In particular, a spaced-massed differential effect on long-lasting memory recently has been established for the conditioned fear-potentiated startle effect in rats (a mammalian model system). In the fear-potentiated startle paradigm, memory is inferred from an increase in startle amplitude in the presence of a conditioned stimulus (CS) that has been previously paired with footshock. Massed training in rats (4-CS-shock pairings with a 10-second intertrial interval) produces essentially no transcription-dependent memory whereas spaced training (4 pairings with an 8-minute intertrial interval) produces significant transcription-dependent memory (FIG. 6) (Josselyn et al., Society for Neurosci., 24: 926, Abstract 365.10 (1998)). Moreover, overexpression of CREB activator, delivered to the amygdala via viral vector technology, enhances memory from massed training in a manner directly analogous to that observed in Drosophila (FIG. 7) (Josselyn et al., Society for Neurosci., 24: 926, Abstract 365.10 (1998)). These data demonstrate a CREB-dependent spaced-massed differential with which to identify mammalian CMGs.

Hence, these specific training protocols are expected to yield CMGs in animals, such as mammals, similar to the CMGs identified in Drosophila. The term "animal", as used herein, includes mammals, as well as other animals, vertebrate and invertebrate (e.g., birds, fish, reptiles, insects (e.g., Drosophila species), Aplysia). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminents (e.g., cows, pigs, horses).

To identify the CMGs in non-human animals (particularly non-human mammals, other vertebrates and invertebrates), DNA probes are synthesized using RNA extracted from brain tissues of spaced- or massed-trained non-human animals according to methods generally known in the art (see, e.g., Sambrook et al., Eds., Molecular Cloning: A Laboratory Manual, 2nd edition, Cold Spring Harbor University Press, New York (1989); and Ausubel et al., Eds., Current Protocols In Molecular Biology, John Wiley & Sons, New York (1997)). These probes can be labeled with a detectable marker. In a particular embodiment, DNA probes are synthesized using RNA extracted from the amygdala of spaced- or massed-trained animals and, if required, labeled with a detectable marker. A variety of detectable markers and labeling methods are known in the art, including fluorescent, chemiluminescent, biotin, radioactive, enzymatically detected and immunologically detected markers (see, e.g., Sambrook et al., Eds., Molecular Cloning: A Laboratory Manual, 2nd edition, Cold Spring Harbor University Press, New York (1989); and Ausubel et al., Eds., Current Protocols In Molecular Biology, John Wiley & Sons, New York (1997)). RNA is extracted from brain tissues, such as the amygdala, according to methods available in the art. Spaced- and massed-training of animals are conducted using methods generally known in the art (see, e.g., Josselyn et al., Society for Neurosci., 24: 926, Abstract 365.10 (1998); Cassella and Davis, Physiol. Behav., 36:377-383 (1986); Guzowski et al., Proc. Natl. Acad. Sci. USA, 94:2693-2698 (1997); Lamprecht et al., J. Neuroscience, 17(21):6443-6450 (1997); Bourtchuladze et al., Cell, 79:59-68 (1994); and Kogan et al., Curr. Biol., 7:1-11 (1996), which are incorporated herein by reference). This complex probe mixture then is hybridized onto microarray chips containing DNA sequences (target DNA sequences) of genes of the genome of the animals (see, e.g., U.S. Pat. No. 5,445,934; and Ramsay, Nature Biotechnology, 16:40-44 (1998), which are incorporated herein by reference). The signal from hybridized DNA probes is amplified and detected according to methods generally known in the art (see, e.g., Sambrook et al., Eds., Molecular Cloning: A Laboratory Manual, 2nd edition, Cold Spring Harbor University Press, New York (1989); and Ausubel et al., Eds., Current Protocols In Molecular Biology, John Wiley & Sons, New York (1997)). For example, hybridization (the signal from the hybridized probe) can be detected using fluorescence assays or mass spectrometry. Methods using optical fibers, diode array detection, chemiluminescence/luminescence, latex bead agglutination, direct electrical charge change detection (CCD) and piezoelectric readout can also be used. The signal transformation algorithm described above is used to calculate gene expression levels between spaced- and massed-trained groups. A statistically significant difference in transcript level between spaced- and massed-trained groups for a specific gene identifies a candidate memory gene. Statistical comparison (DNA chip comparison) between spaced- and massed-trained groups can be made using the signal transformation algorithms described above.

In addition to statistical comparisons between spaced- and massed-trained groups, CMGs can be identified from DNA chip comparisons (statistical comparisons) between animals trained using other pairs of experimental protocols. The experimental group is trained under conditions sufficient to induce transcription-dependent memory and the control group is trained under conditions that are not sufficient to induce transcription-dependent memory. The significant difference between any two experimental protocols is in the induction of transcription-dependent memory. The significant difference between any two experimental protocols to be compared is the induction of transcription-dependent memory in the experimental group and the absence of transcription-dependent memory in the control group.

Pairs of experimental protocols that primarily differ in the induction of transcription-dependent memory are known the art. For example, a pair of experimental protocols that primarily differ in the induction of transcription-dependent memory can consist of a spaced training protocol and a massed training protocol. In this embodiment, training an animal using a spaced training protocol is sufficient to induce transcription-dependent memory in the animal. Training an animal using a massed training protocol is not sufficient to induce transcription-dependent memory. As another example, a pair of experimental protocols that primarily differ in the induction of transcription-dependent memory can consist of training a normal (wildtype) animal using a shuttle-box avoidance protocol (particularly a one-trial shuttle-box avoidance protocol) and training an animal in which the fornix is surgically lesioned using the shuttle-box avoidance protocol (Taubenfeld et al., *Nat. Neurosci.*, 2(4):309-310 (1999)). In this embodiment, transcription-dependent memory is induced in the normal (wildtype) animal. Transcription-dependent memory is not induced in the animal in which the fornix is surgically lesioned. As a further example, a pair of experimental protocols that primarily differ in the induction of transcription-dependent memory can consist of training an animal using a contextual fear conditioning protocol (particularly a one-trial contextual fear conditioning protocol) and training an animal habituated to the training chamber before contextual fear conditioning using the contextual fear conditioning protocol (Imprey et al., *Nat. Neurosci.*, 1(7):595-601 (1998)). In this embodiment, transcription-dependent memory is induced in the animal that had not been habituated to the training chamber prior to contextual fear conditioning. Transcription-dependent memory is not induced in the animal habituated to the training chamber before contextual fear conditioning. Other pairs of experimental protocols can readily be identified by those skilled in the art.

DNA probes are synthesized using RNA extracted from the brain tissues, such as the amygdala and hippocampus, of animals trained using pairs of experimental protocols, as described herein, and, if required, labeled with a detectable marker. The DNA probe mixtures then are hybridized onto microarray chips containing DNA sequences (target DNA sequences) of genes of the genome of the animals. A statistical comparison is made by comparing the DNA chip data between the two experimental protocols using the signal transformation algorithms described above.

The statistical procedures herein can be used to detect differences in transcript levels between trained and untrained (naïve) groups. Accordingly, candidate plasticity genes (CPGs) can be identified from DNA chip comparisons (statistical comparisons) between trained versus untrained (naïve) animals. Transcripts that are differentially regulated in this class will include the CMGs, along with any other genes that are transcriptionally responsive in a "nonassociative" manner to the general training conditions (e.g., presentations of odors, electroshock or any other experiential aspects of the training protocol). Some nonspecific transcriptional responses occur simply when an animal is placed in a novel environment or when the animal is exposed to a stimulus alone or unpaired in time. These transcriptional changes may result from general (nonspecific) increases in neuronal activity or reflect other forms of learning/memory formation that are not related to the general training conditions.

CPGs from *Drosophila* determined from statistical analysis using the signal transformation algorithm in which an average difference value below 10 for a given gene is deleted, from the spaced versus naïve comparison (24-hour memory), are presented in Table 3. CPGs from *Drosophila* determined from statistical analysis using the signal transformation algorithm in which a negative average difference value for a given gene is zeroed, from the spaced versus naïve comparison (24-hour memory), are presented in Table 4.

TABLE 3

Statistical Candidate Plasticity Genes, derived from statistical analysis (delete avg. diff. values <10), from the spaced versus naïve comparison (24-hour memory).

ribosomal protein S6 (rps6)
hu-li tai shao (hts) mRNA
ribosomal protein S3/AP endonuclease DNA repair protein mRNA
gurken gene
atonal protein mRNA
cytoplasmic dynein intermediate chain (Cdic) gene
glyceraldehyde-3-phosphate dehydrogenase-1 gene
glyceraldehyde-3-phosphate dehydrogenase-2 gene
50 kDa protein F1 gene
Dmras85D gene
serine protease (SER1 and SER2) genes
myosin light chain 2 (MLC2) mRNA
carboxylesterase 6 and P (Est-6 and Est-P) genes
annexin IX mRNA
proteasome (PROSA-28.1.1.) mRNA
laminin B2 gene
octopamine receptor mRNA
A2 component of diphenol oxidase (Dox-A2) gene
homolog of RAD6 (DHR6) mRNA
Mov34 protein mRNA
glu-prolyl tRNA aminoacyl synthetase mRNA
G protein-coupled receptor kinase (GPRK-1) mRNA
optomotor-blind mRNA
profilin (chickadee) mRNA
transcription factor IIB (TFIIB) mRNA
glutathione S-transferase-related protein mRNA
trypsin-alpha, -beta and -epsilon genes
trypsin-alpha, -beta and-epsilon genes
catalase gene
proteasome subunit (1(3)73Ai) gene
Canton S pheromone-binding protein-related protein PBPRP-2 mRNA
transcription initiation factor TFIID 28 kDa subunit mRNA
glutathione-dependent formaldehyde dehydrogenase gene
cofilin/actin depolymerizing factor homolog mRNA
N-ethylmaleimide-sensitive fusion protein mRNA
ribosomal protein DL11 mRNA
rfc40 protein, Rop protein (Rop), and small GTP binding protein
PROS-Dm25g gene for proteasome
DmTnC 41C mRNA for troponin-C
WM6 mRNA
mRNA for 40S ribosomal protein S12
mRNA for mitochondrial ATPase synthase
genes mst 355a and 355b for male accessory gland secretory protein
Pgk gene for phosphoglycerate kinase
*D. melanogaster* ribosomal protein 15a (40S subunit).
eye color protein (garnet) mRNA
cysteine proteinase-1 (CP1) gene
calcium-binding protein (SCP1) mRNA
cytochrome P450 (CYP4D2) gene
alpha NAC (oxen) gene, complete cds; and G76C pseudogene
alpha NAC (oxen) gene, complete cds; and G76C pseudogene
kinesin-related protein (costal-2) mRNA
transcriptional co-repressor SIN3A (Sin3A) mRNA
chitinase (CHT2) gene
mRNA for rab-related protein 4.
mRNA for still life type 1
cell adhesion molecule encoding (nrm) gene
phosphoglycero mutase (Pglym78) gene
receptor guanylyl cyclase (DGC1) mRNA
(W-IR1 mutation) I factor DNA
(W-IR1 mutation) I factor DNA
Fw repetitive element putative reverse transcriptase
Fw repetitive element putative reverse transcriptase
RNA polymerase II second largest subunit upstream (DmRP 140)
ecdysone-inducible membrane (IMP-L1) gene
mdg1het, integrase {MDG1 retrotransposon}

TABLE 3-continued

Statistical Candidate Plasticity Genes, derived from statistical analysis (delete avg. diff. values <10), from the spaced versus naïve comparison (24-hour memory).

Dacp-1 = cuticle protein
glutamate decarboxylase mRNA
HeT-A element 23Zn-1.
(zeste-white 4) mRNA
Dachshund (dachshund) mRNA
Hk protein mRNA
soluble guanylyl cyclase beta subunit (dgcb1)
cytochrome P450 (Cyp4g1) mRNA
alpha esterase (aE10) gene
vacuolar ATPase subunit A (vha68-2) gene
fatty acid desaturase mRNA
wunen gene
Rga and Atu genes
kinesin-73 mRNA
MCM5 homolog (DmMCM5) mRNA
kinesin like protein 67a mRNA
sperm-specific protein component (dj) mRNA
DNA sequence (isolate CBS) for 18S rRNA (3'end), 5.8S rRNA and 28S rRNA
nmr mRNA for DNMDAR-I
mRNA for angiotensin-converting enzyme-like protein
mRNA for histone H4
mRNA for ladybird late homeodomain transcription factor
colt gene
mRNA for ATP synthase subunit gamma
mRNA for 3-hydroxyacyl-CoA-dehydrogenase type II

TABLE 4

Statistical Candidate Plasticity Genes, derived from statistical analysis (negative avg. diff. value is zeroed), from the spaced versus massed comparison (24-hour memory).

daughterless protein (da)
steroid receptor (FTZ-F1B)
POU domain protein (pdm-1)
bithorax complex (BX-C)
nuclear hormone receptor superfamily(DHR96)
transcriptional co-repressor SIN3A (Sin3A)
mRNA for histone H4
mRNA for ladybird late homeodomain
RAD6 (DHR6)
putative serine protease (easter)
serine protease (SER1 and SER2) genes
proteasome (PROSA-28.1.1.)
Mov34 protein
trypsin-alpha, -beta and -epsilon
trypsin-alpha, -beta and -epsilon genes
proteasome subunit (l(3)73Ai) gene
20S proteasome alpha subunit PSMA5 gene
snake locus mRNA for serine protease
D. melanogaster PROS-Dm25g gene for proteasome
male accessory gland secretory protein (serpin)
serine protease SER4 precursor (Ser4)
cysteine proteinase-1 (CP1) gene
clone 6 serine protease mRNA
Drosophila melanogaster dishevelled mRNA, complete cds.
Dmras85D gene, exon 3
G protein-coupled receptor kinase (GPRK-1) mRNA
rfc40 protein, Rop protein (Rop), and small GTP binding protein
tyrosine kinase, partial sequence
mRNA for rab-related protein 4
mRNA for rab-related protein 3
GDP dissociation inhibitor homologue (dGDI) mRNA
(zeste-white 4) mRNA
phosphoinositide 3-kinase, Dp110
phosphatase 2A catalytic subunit
fasciclin III mRNA
annexin IX mRNA
alpha-methyldopa hypersensitive gene l(2)amd
GS2 mRNA for glutamine synthase
GS1 mRNA for glutamine synthase TABLE 4-continued Statistical Candidate Plasticity Genes, derived from statistical analysis (negative avg. diff. value is zeroed), from the spaced versus massed comparison (24-hour memory).

mRNA for dopamine receptor
eye color protein (garnet) mRNA, clathrin like
cell adhesion molecule encoding (nrm) gene
Nrv 2.2 neuron surface antigen 2 (Nrv2) mRNA
R vacuolar ATPase subunit A (vha68-2) gene
mRNA for DNMDAR-I
AcTr66B gene for actin-related protein
DmTnC 41C mRNA for troponin-C
kinesin-related protein (costal-2) mRNA
microtubule associated protein (asp) mRNA
cytoplasmic dynein intermediate chain (Cdic) gene The present invention provides methods of identifying a gene or genes involved in transcription-dependent memory (particularly long term memory) comprising (a) training non-human animals (particularly non-human mammals, other vertebrates and invertebrates) under conditions sufficient to induce transcription-dependent memory (particularly long term memory) in the animals; (b) extracting RNA from brain tissue (such as from amydala, hippocampus) of the animals trained in step (a); (c) synthesizing DNA probes using the RNA extracted in step (b); (d) exposing the DNA probes synthesized in step (c) to microarray chips containing DNA sequences from genes of the genome of the animals under conditions appropriate for hybridization of the DNA probes to complementary DNA sequences on the microarray chips, wherein a signal is produced upon hybridization of the probes to complementary DNA sequences; (e) detecting the signal produced in step (d); and (f) performing a statistical comparison between the signal detected in step (e) and the signal detected in a control.

In one embodiment, the control is obtained according to a method comprising (i) training non-human control animals (particularly non-human mammals, other vertebrates and invertebrates) under appropriate conditions, wherein the conditions are insufficient to induce transcription-dependent memory in the control animals; (ii) extracting RNA from brain tissue of the control animals trained in step (i); (iii) synthesizing DNA probes using the RNA extracted in step (ii); and (iv) exposing the DNA probes synthesized in step (iii) to microarray chips containing DNA sequences from genes of the genome of the animals under conditions appropriate for hybridization of the DNA probes to complementary DNA sequences on the microarray chips, wherein a signal is produced upon hybridization of the probes to complementary DNA sequences. The experimental conditions of step (a) and step (i) constitute an (experimental) treatment pair. The significant difference between the experimental conditions of step (a) and step (i) is in the induction of transcription-dependent memory.

In a second embodiment, the control is obtained according to a method comprising (i) extracting RNA from brain tissue of non-human control animals; (ii) synthesizing DNA probes using the RNA extracted in step (i); and (iii) exposing the DNA probes synthesized in step (ii) to microarray chips containing DNA sequences from genes of the genome of the animals under conditions appropriate for hybridization of the DNA probes to complementary DNA sequences on the microarray chips, wherein a signal is produced upon hybridization of the probes to complementary DNA sequences. In this embodiment of the control, the control animals are naïve (untrained) animals.

As used herein, a control animal is an animal that is of the same species as, and otherwise comparable to (e.g., similar age, sex), the animal that is trained under conditions sufficient to induce transcription-dependent memory formation in that animal.

Transcription-dependent memory can be induced using specific experimental conditions. In one embodiment, transcription-dependent memory is induced in a non-human animal using a spaced training protocol for the fear-potentiated startle response. In a second embodiment, transcription-dependent memory is induced in a non-human animal using a shuttle-box avoidance protocol. In a third embodiment, transcription-dependent memory is induced in a non-human animal using a contextual fear conditioning protocol.

The present invention will now be illustrated by the following examples, which are not to be considered limiting in any way.

EXAMPLES

Example 1

Isolation of nalyot$^{P1}$

An X-linked PlacW transposon (Bier et al., *Science*, 240(4854):913-916 (1988)) was mobilized to generate 2,182 transposant strains with independent insertions on the second and third chromosomes (cf. Boynton and Tully, *Genetics*, 131:655-672 (1992); Dura et al., *J. Neurogent.*, 9:1-14 (1993)). Three-hour memory after a single training session of Pavlovian olfactory learning was quantified with one performance index (PI) for each of these transposant strains. N=4 PIs then were generated for those strains that scored 70% or less of a wild-type parental strains [w$^{1118}$ (CS10)]. At this stage of the screen, 93 mutant strains yielded mean three-hour memory scores 70% wild-type or less. Each of these candidate mutant strains then was outcrossed for five generations to the parental strain to equilibrate their (heterogeneous) genetic backgrounds. When three-hour memory again was quantified (N=4 PIs) in these outcrossed strains, only eight of the 93 candidate mutants still yielded mean scores <70% wildtype. Finally, "task relevant" sensorimotor tasks were assayed in these eight mutant strains. All eight showed normal shock reactivity; four, G$_B$335 and E$_J$51, E$_J$220 and E$_S$152, showed significantly reduced olfactory acuity (Boynton and Tully, *Genetics*, 131:655-672 (1992); Dura et al., *J. Neurogent.*, 9:1-14 (1993). [G$_B$335, now named dare, has been studied further and shows preferential expression in antenna (Freeman et al., *Development*, 126: 4591-4602 (1999)]. The remaining four mutant strains displayed normal sensorimotor responses and were named latheo (Boynton and Tully, *Genetics*, 131:655-672 (1992); Pinto et al., *Neuron*, 23:45-54 (1999); Rohrbough et al., *Neuron*, 23:55-70 (1999), linotte (Dura et al., *J. Neurogent.*, 9:1-14 (1993); Bolwig et al., *Neuron*, 15:829-842 (1995); Simon et al., *Mech. Dev.*, 76:42-55 (1998), golovan and nalyot.

Example 2

Cloning and Characterization of nalyot Genomic Region

Figure 8:
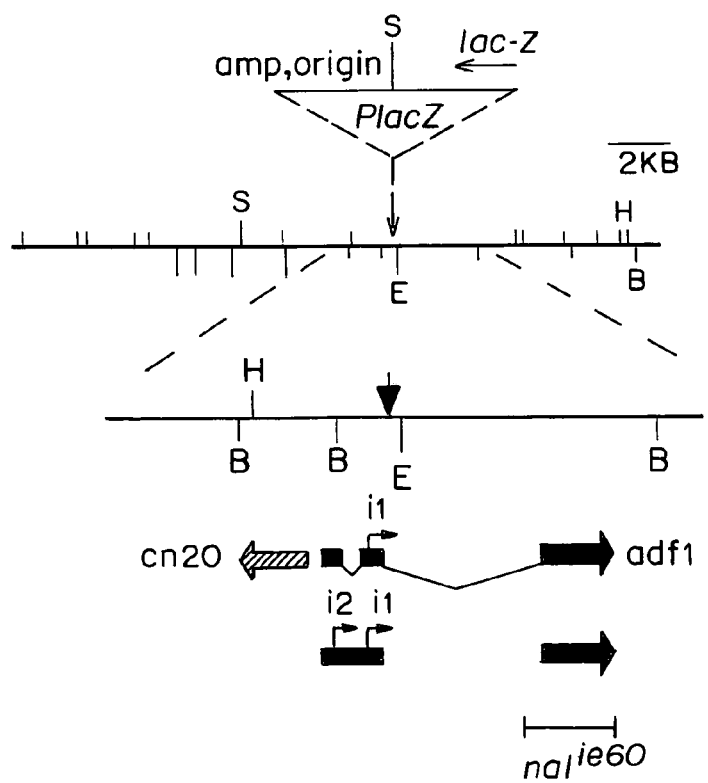
FIG. 8 depict molecular maps of the adf1 genomic region.

The PlacW transposon includes a unique SacII restriction site followed by the bacterial origin of replication and ampicillin resistance gene (FIG. 8). Digestion of nalyot (nal) genomic DNA with SacII ligation under dilute conditions and bacterial transformation allowed plasmid rescue of a 9.4 kb SacII restriction fragment along with flanking DNA from the genomic region. Chromosome in situs and southern blotting experiments verified that this fragment co-mapped to the P-insertion site. The radiolabeled rescue fragments were used to screen one million plaques of a lambda-DashII *Drosophila* Can-S genomic library (Stratagene). Isolation, subcloning and restriction analysis of 10 independent genomic clones led to the construction of a 35 kb map spanning the genomic region around the P-element insertion site (FIG. 8).

Intron/exon maps of the adf1 and cn20 transcription units are shown in FIG. 8. The nal$^{P1}$ element (arrow) is inserted within an intron of the adf1 transcription unit, 147 bp downstream of the splice donor site. The adf1 gene encodes a transcription factor distantly related to the myb family (England et al., *Proc. Natl. Acad. Sci. USA*, 89:683-687 (1992)) and is alternatively spliced into (at least) two mRNAs. i1 and i2 correspond to two potential translation start sites. Two additional introns of about 3.5 kb and 59 bp appear to be spliced constitutively and separate the remainder of the adf1 transcription unit into 274 bp and 1,013 bp exons. The cn20 gene is novel and produces a single, unspliced transcript that can encode a 395 amino acid protein. The extent of the genomic deletion in nal$^{le60}$ is indicated. Restriction sites: B, BamHI; E, EcoRI; H, HindIII; S, SacII.

Example 3

Northern Blot Analysis of adf1 and cn20 In Mutant nal$^{P1}$ and Wildtype Flies and cDNA Isolation Total RNA from whole adult flies, adult heads or adult bodies was isolated with the TriZOL reagent (BRL). The poly(A) fraction was subsequently purified with oligo(dT) cellulose (Collaborative Research) or magnetized oligo(dT) beads (Dynal). Purified poly(A) RNA was fractionated by formaldehyde-agarose gel electrophoresis and transferred to a ZetaProbe nylon membrane (BioRad) in 10×SSC. The RNA on the dried membrane was fixed by UV-crosslinking at 2,500 ujoules (Stratalinker). For initial identification of transcript classes, membrane strips were probed overnight with radiolabeled genomic DNA fragments in high stringency Church and Gilbert Buffer, washed extensively and exposed to Kodak BioMax film.

Selected probes were hybridized to two *Drosophila* adult head cDNA libraries, a lambda gt11 bacteriophage adult head library (Salvaterra) and a pJG4-5 plasmid library (Roshbash). From these two libraries, a total of eleven clones, corresponding to two independent transcription units, were isolated and evaluated by restriction analysis. Ten clones corresponded to the adf1 transcription unit. Restriction-mapping and sequence analysis of a subset of these revealed a common 3' end processing site and heterogeneity at the 5' end. The 5' heterogeneity reflected the partial splicing of intron 1 (114 bp) and, perhaps, incomplete first strand synthesis. One clone, cn20, corresponded to an independent, neighboring transcription unit.

To quantify the effect of the P-insertion on adf1 and cn20 RNA levels, Northern blots derived from nal$^{P1}$ and wildtype heads or bodies were analyzed as above with radiolabeled probes corresponding to adf1, cn20 and a control RNA rp49.

Relative to control levels of rp49 RNA, cn20 mRNA expression levels in both heads and bodies were similar in wildtype and mutant flies. In contrast, adf1 mRNA expression levels were reduced by at least two-fold in mutant heads and bodies.

Example 4

Antibody Production

The entire ADF1 open reading frame was inserted into the pET30(a) expression vector (Novagen) as a C-terminal fusion. Robust IPTG induction of ADF1 fusion protein was obtained in transformed BL21 bacteria. The majority of induced protein was in the insoluble, inclusion body fraction and this fraction (isolated 3 hours after induction) was enriched nearly 85% for the ADF1 fusion protein. This fraction was washed extensively with PBS and used directly as antigen. Mouse polyclonal and monoclonal antibodies were obtained by standard procedures (Harlow and Lane, *Antibodies. A Laboratory Manual*, Cold Spring Harbor Laboratory Press, Plainview, N.Y. (1998)). Three mice were inoculated with 50 μg of the inclusion body fraction (in complete Freund's adjuvant), then boosted every two weeks with 50 μg of inclusion body fraction in incomplete Freund's adjuvant. All three mice showed robust immune responses; one was sacrificed for hybridoma fusions. Of 800 candidate hybridoma lines, 17 showed a response in ADF1 dot-blot analyses. Subsequent evaluation of the 17 lines by western blotting and immunochemical assays led to the isolation of ten monoclonal lines, including MAb ADF1-8 and MAb ADF1-17.

Example 5

Western Blot Analysis of ADF-1 Protein Levels In Mutant nal$^{P1}$ and Wildtype Flies Frozen heads or bodies were isolated as previously described (Yin et al., *Cell*, 79:49-58 (1994)), and extracts were prepared by homogenizing 100 μl of frozen head powder in 500 μl of RIPA buffer. Protein concentrations were determined by the Bio-Rad protein assay. Protein samples were denatured in standard loading dye, separated by SDS-PAGE and transferred electrophoretically at 100 mA for 2 hours to a nitrocellulose membrane (Bio-Rad). Each membrane was blocked overnight at 4° C. in PBST+ 5% milk, then incubated for 1-2 hours with primary antibody in PBST+5% milk. Primary antibodies used were mouse polyclonal sera against adf1 (1:1000), mouse monoclonal supernatant (MAb Adf1-17) against adf1 (1:20), mouse monoclonal supernatant against TBP (1:5), and mouse monoclonal ascites against a-tubulin (1:50,000) (Sigma). The membrane was washed extensively in PBST and incubated for 1-2 hours with HRP-conjugated anti-IgG secondary antibody (Bio-Rad; 1:500). Following extensive washing in PBST, the conjugated products were visualized by enhanced chemiluminescence (Pierce SuperSignal ULTRA Substrate) and autoradiography.

Relative to control levels of two other proteins (TATA-binding protein and alpha-TUBULIN), ADF1 expression was reduced at least two-fold in mutant flies.

Example 6

Comparison of DNA Chip Data Sets Between Wildtype Flies and a Single-Gene Mutant, nalyot DNA chip data sets between normal (wildtype) flies and a single-gene mutant, nalyot were compared. The nalyot mutant was shown to have normal memory after massed training, but LTM was not induced by spaced training. Moreover, the nalyot mutation was identified as a transposon insertion in the Adf1 gene, the effect of which is to reduce the amount of Adf1 transcript and protein in mutant fly heads.

When all baseline values were set to zero and the data then were analyzed, no significant difference between wildtype flies and nalyot mutants was detected for the Adf1 gene. However, when baseline values of 10 or less were eliminated from the analysis (rather than set to zero), a significant effect on Adf1 transcription was detected, which corroborated the results obtained by Northern analysis, as described in Example 3. This result constitutes a significant verification for the statistical approach in which average difference values below 10 are deleted from the data set.

Example 7

Quantitative Polymerase Chain Reaction

A given group of flies is subjected to a particular training protocol (spaced or massed) and stored in regular food vials after training. Twenty four hours after training, flies from different groups of a given training protocol (spaced or massed) are collected into a single 50 ml Falcon tube and quick-frozen in liquid nitrogen. The heads of frozen flies are separated from their bodies by vigorous mechanical shaking. Frozen and separated body parts then are sifted through a series of sieves, ultimately to obtain a homogeneous population of fly heads.

Combined heads from a training group (spaced or massed) are separated into eight groups. Each group of heads then is ground into a powder with mortar and pestal. The powder is transferred to 5 ml of Trizol solution (Gibco) and stored at −70° C. overnight.

The frozen Trizol/fly powder solution then is thawed. 2 ml of chloroform is added. The mixture is centrifuged at 3,500 rpm for 10 minutes at 4° C. The extracted RNA (in aqueous layer) is decanted to a fresh tube, and 1.4 ml of isopropanol is added.

For QPCR, aliquots of the above solution are spun at 8,000 rpm for 20 minutes at 4° C. Isopropanol is decanted, and the pellet is washed 1× in 70% ethanol. The pellet is resuspended in 100 μl of $H_2O$ and an equal volume of phenol/chloroform (Gibco) is added. The solution is centrifuged at 14,000 rpm for 5 minutes at 4° C. The top aqueous layer is decanted to a fresh tube. 200 μl of ice-cold ethanol is added, along with 6 μl of 3 M sodium acetate. The solution is incubated at −20° C. for at least 20 minutes.

The solution is then centrifuged at 14,000 rpm for 20 minutes at 4° C. The pellet is resuspended in 20 μl of $H_2O$ and subjected to RQ1 Rnase free DNAse (Promega). RNA concentration is determined.

First-strand cDNAs then are synthesized from 1 μg of the DNAse-free RNA samples, and the QPCR assay is performed according to Perkin Elmer Biosystems protocols, using the 7700 ABI Prism with "CYBR" cybergreen flourescence detection.

Example 8

Statistical Candidate Memory Gene, C/EBP

The following C/EBP primers, designed by Quantagene (Paris, France), were used in QPCR experiments: 5'-AGAC-TACCGATGCGAACAAC-3' (SEQ ID NO:1) and 3'-GTC- CCTGAACTGGTCGTCTA-5' (SEQ ID NO:2), yielding an expected fragment of 221 bp in size.

For C/EBP data, 8 replicated RNA extractions were obtained from approximately 10,000 heads of flies 24 hours after they were subjected to spaced or to massed training. QPCR reactions for each RNA extraction were run in triplicate in accordance with the method outlined in Example 7.

Results for each C/EBP reaction were normalized for RNA amounts against a paired QPCR reaction for TF2D, a control gene which shows no transcriptional changes in these contexts.

Analyzed this way, the mean number of cycles required for C/EBP amplification to reach the critical value was 21.86±0.56 for the spaced group and 23.78±0.56 for the massed group. It took fewer amplification cycles for the spaced group to reach the critical value, indicating a higher concentration of C/EBP at the beginning of the PCR amplification.

Figure 5:
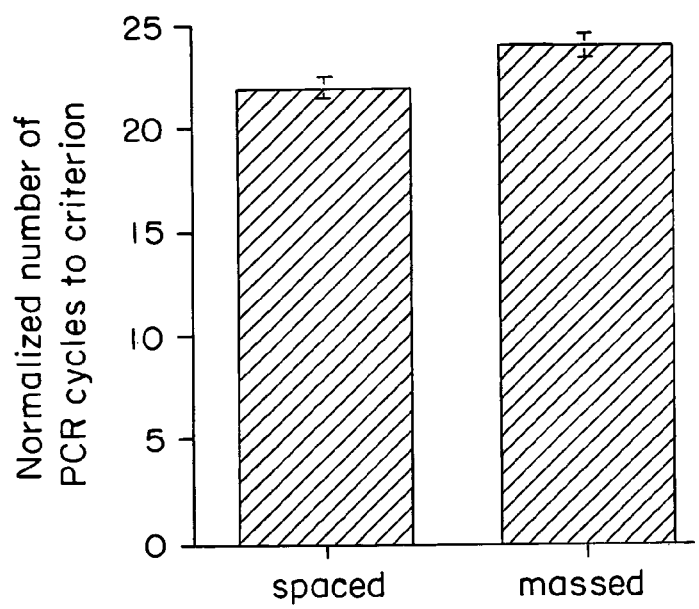
FIG. 5 is a bar graph showing the results from a quantitative polymerase chain reaction (QPCR) experiment. The results confirm the differential effect of spaced versus massed training on the C/EBP gene.

These data indicate C/EBP levels were 3.78-fold higher in the spaced training group than in the massed training group (FIG. 5). The experimental results confirm that there is a significant difference for C/EBP (called slow border cells, slobo in *Drosophila*) transcripts isolated from spaced-versus massed-trained flies. Genetic manipulation of C/EBP in mice enhances long-term memory (Sterneck et al., *Proc. Natl. Acad. Sci. USA*, 95(18):10908-10913 (1998)), and molecular manipulation of C/EBP in Aplysia blocks long-term facilitation (a cellular substrate for long-term memory of sensitization) (Alberini et al., *Cell*, 76:1099-1114 (1994)). Therefore, confirmation of C/EBP as a CMG herein constitutes a significant verification that this DNA chip approach can be used in identifying transcripts involved in memory.

Example 9

Training Apparatus

Experimentally naïve male Sprague-Dawley rats (300-350 g) were trained and tested in five identical Plexiglas and wire-mesh cages (8×15×15 cm) housed in a sound-atrenuated chamer (Cassella and Davis, *Physio. Behav.*, 36:377-383 (1986)). The startle-eliciting stimulus was a 105 dB, 50-ms burst of white noise (rise-decay time 5 ms), against a background white noise of 55 dB. A 3.7-s light CS was produced by an 8-W fluorescent lightbulb (rise-decay time, 100 µs; BCO foot-lamberts intensity). The floor on each cage consisted of four stainless steel bars, through which a 0.5-s 0.6 or 0.3 mA scrambled foot shock could be delivered.

Example 10

Behavioral Training Procedures

On each of two days before all training, rats were placed in the startle chambers and 15 minutes later presented with 15 startle stimuli. On the single training day for Exp. 1, animals were placed in the startle chamber and 5 minutes later received 4 light-shock pairings with one of the following intertrial intervals (ITIs) (3-seconds, 5-seconds, 10-seconds, 15-seconds, 2-minutes or 8-minutes). Five minutes following the last light-shock pairing, animals were returned to their home cages. Paired massed and spaced training were similarly conducted except that the ITI between the 4 light-shock pairings was 10 seconds and 8 minutes, respectively. Explicitly unpaired massed training trials consisted of massed presentations of the light (4, ITI of 10 seconds) followed 4 minutes later by massed presentations of the shock (4, ITI of 10 seconds).

Example 11

Long Term Memory Testing

Forty-eight hours following training, rats were placed in the startle apparatus and received 30 startle-eliciting stimuli alone followed by 60 startle-eliciting stimuli, half of which occurred 3.2 seconds after the onset of the 3.7 seconds light (Light-Noise trial) and half of which were presented in darkness (Noise Alone trial). The order of the two trial types was irregular. All startle stimuli were presented at an interstimulus interval of 30 seconds. Fear-potentiated startle difference scores, used as an index of LTM, were calculated by subtracting the average startle amplitudes produced by the 30 Noise Alone trials from the average startle amplitudes produced by the 30 Light-Noise trials.

Example 12

Short Term Memory Testing

Short term memory (STM) testing was similar to LTM testing except that it occurred 15 or 40 minutes following training. Twenty Noise Alone stimuli were followed by 15 Light-Noise stimuli and 15 Noise Alone stimuli intermixed. Fear-potentiated startle scores were calculated by subtracting the average Noise Alone score from the average Light-Noise score and used as an index of STM.

Example 13

Surgery

Rats were pre-treated with atropine sulfate (0.4 mg/kg, ip), anesthetized with sodium pentobarbital (60 mg/kg, ip) and placed in a standard stereotaxic instrument. A Hamilton microsyringe (10 µl) mounted in an infusion pump was used for infusions. Bilateral microinjections (2 µl) were delivered over 10 minutes through a 30 gauge cannulae aimed at the lateral nucleus of the amygdala (coordinates AP=−2.8, L=±5.2, DV=−8.5 below the surface of the skull) or caudate nucleus (co-ordinates AP=+0.2, L=±3.0, DV=−6.0) according to Paxinos and Watson, *The Rat Brain in Stereotaxic Coordinates*, Academic, Syndney, Australia (1986). Infusion cannulae were left in place an additional 10 minutes to ensure diffusion.

Example 14

Virus Preparation

CREB and mCREB cDNAs (obtained from M. E. Greenberg, Harvard University) and LacZ were inserted into the HSV amplicon HSV-PrpUC and packed using the helper 5 dl 1.2 (Lim et al., *Biotechniques*, 20:460-469 (1996); Keve et al., *Neuroscience*, 79:435-447 (1997)). Virus was purified on a sucrose gradient, pelleted and resuspended in 10% sucrose. The average titer of the recombinant virus stocks was $4.0 \times 10^7$ infectious units/ml and was similar for HSV-CREB and HSV-mCREB. Transgene expression was regulated by the constitutive promoter for the HSV immediate-early gene IE 4/5.

Example 15

Immunochemistry

Rats were overdosed with chloral hydrate and perfused with 50 ml PBS followed by 250 ml 4% paraformaldehyde in PBS. The brains were cryoprotected and cut on a microtome (40 μm sections), and immunocytochemistry was performed on free-floating sections. Brains infected with HSV-LacZ were reacted for β-galactosidase and counterstained with neutral red (according to Lim et al., *Biotechniques*, 20:460-469 (1996); Keve et al., *Neuroscience*, 79:435-447 (1997)). Briefly, to detect β-galactosidase activity, brain slices were allowed to react for 2 hours in a solution comprised of 3.1 mM potassium ferrocyanide, 3.1 mM potassium ferricyanide, 20 mM $MgCl_2$, 0.1 M PBS and 0.2 mg/ml X-gal (Boehringer-Mannheim).

Analysis of transgene expression in brain infected with HSV-CREB was conducted. Briefly, sections were incubated with 1% $H_2O_2$ and 0.3% Triton-X for 20 minutes, blocked with 1% bovine serum albumin, 2% normal goat serum and 0.3% Titron-X for 30 minutes and incubated with the primary antibody, CREB (1:1000; Upstate Biotechnology, Lake Placid, N.Y.) overnight at 4° C. with constant agitation. Sections were incubated with biotinylated goat-anti rabbit IgG secondary antiserum (1:200 dilution; Vector Laboratories, Burlingame, Calif.) for 2 hours at room temperature. Sections were rinsed and incubated with avidin-biotin peroxidase complex (ABC) reagent (Vector Laboratories). Immunoreactivity was visualized using diaminobenzidine (DAB) reaction.

Example 16

Figure 6:
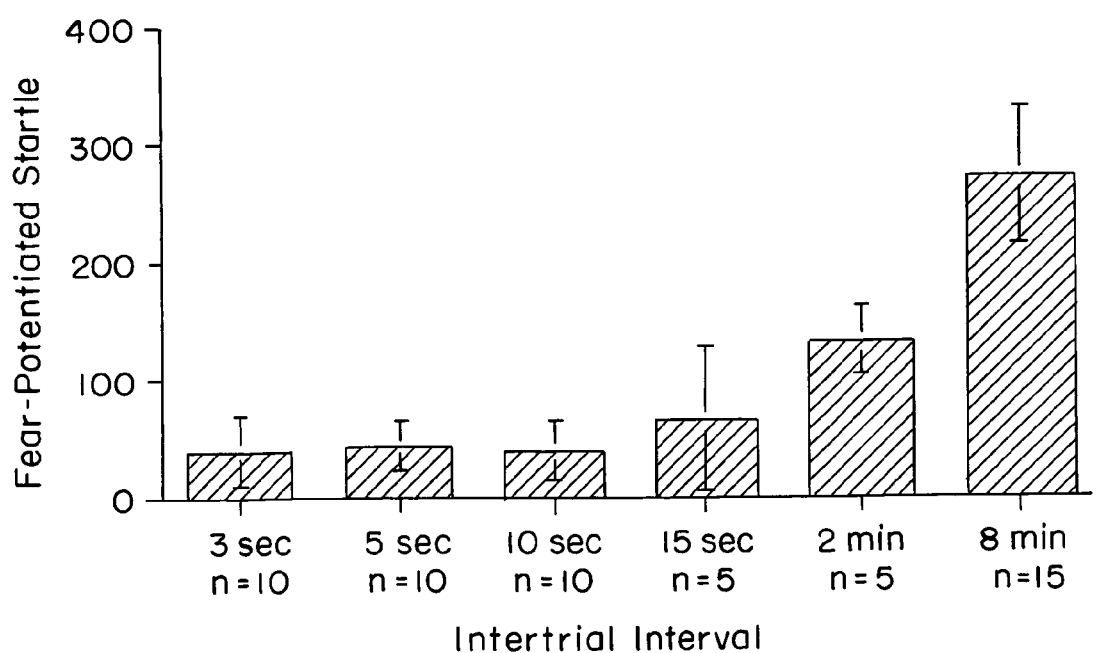
FIG. 6 is a bar graph showing the effect of an intertrial interval (ITI) between fear conditioning training trials in rats on subsequent long-term memory. The results define massed and spaced protocols and show that memory of fear-potentiated startle is better after spaced-training than after massed-training.
Figure 7:
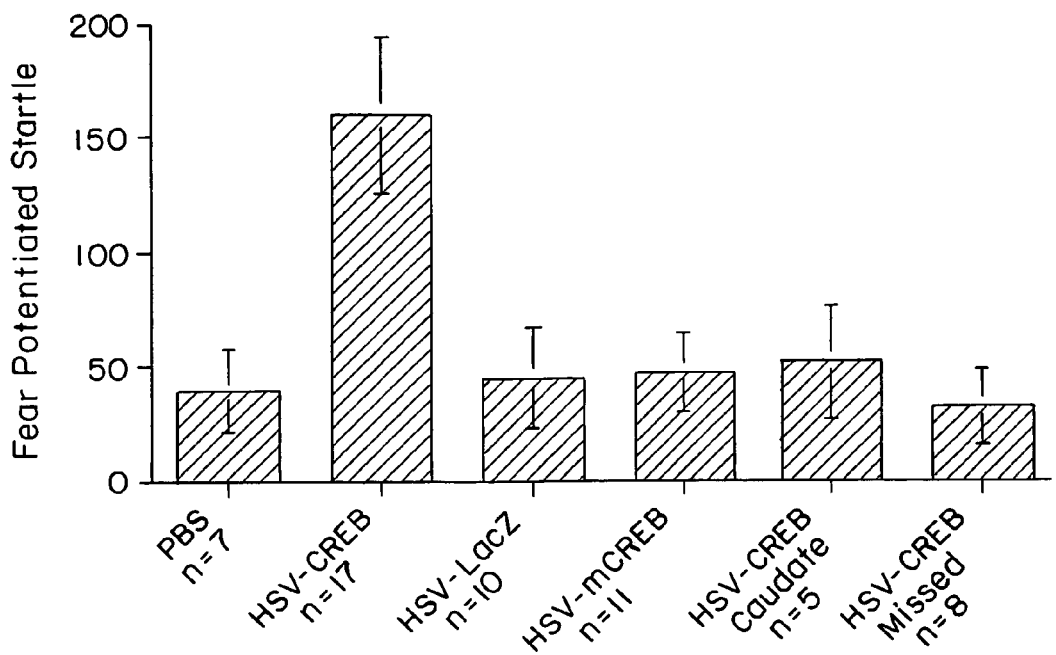
FIG. 7 is a bar graph showing the effect on long term memory of overexpression of CREB activator in the amygdala of rats. The results show that overexpression of CREB activator in the amygdala enhances (increases) memory of fear-potentiated startle in rats after massed training.

Effect of Intertrial interval Between Fear Conditioning Trials on Subsequent Levels of Long Term Memory Mean LTM (±SEM; assessed as fear-potentiated startle difference scores), assessed 48 hours following training that consisted of 4 light-shock pairings with ITIs of 3 seconds, 5 seconds, 10 seconds, 15 seconds, 2 minutes and 8 minutes (n=10, 10, 10, 5, 5, 15, respectively), varied with different ITIs ($F_{1,49}$=3.04, p<0.05). The level of LTM is a linear function of the ITI with longer ITIs producing more robust LTM as shown by a significant linear trend ($F_{1,49}$=7.99, p<0.05). Massed training (3 seconds, 5 seconds, 10 seconds) produces very weak LTM (roughly 50 units). Increasing the rest interval from 10 seconds to 8 minutes yields an increase in LTM as post-hoc Duncan comparisons reveals that 8 min ITI (spaced) produced significantly greater LTM than 10 seconds, 5 seconds and 3 seconds (massed). The results are depicted in FIG. 6.

Example 17

Effect of Infusion of HSV Vectors Into the Basolateral Amygdala and Extra-amygdala Areas Rats infused with HSV-CREB into the basolateral amygdala (n=17) showed significantly greater LTM than rats similarly infused with PBS (n=7), HSV-LacZ (n=10), or HSV-mCREB (n=11) or rats infused with HSV-CREB into brain regions surrounding the basolateral complex of the amygdala (n=8) or into a control region (the caudate; n=5) ($F_{5,52}$=4.99, p<0.001). Post-hoc analysis revealed that the level of LTM in rats that received HSV-CREB infusion into the basolateral amygdala was significantly higher than all other groups.

Reactivity to footshock was not different for animals given HSV-CREB (n=17), HSV-mCREB (n=11), HSV-LacZ (n=10) or PBS (n=7) infusion into the basolateral amygdala prior to massed training ($F_{3,41}$=1.41, p>0.05). Mean shock reactivity was assessed by cage displacement for the 200-ms period after each of the 4 footshocks.

Explicitly unpaired conditioning (in which CS (conditioned stimulus) and US (unconditioned stimulus) are not associated) failed to produce LTM for the association in control rats (n=10) and intra-amygdala infusion of PBS (n=5) or HSV-CREB (n=5) did not change this ($F_{2,17}$=0.44, p>0.05).

Animals that received HSV-CREB 3 days prior to massed training (3d HSV-CREB, n=10) showed greater LTM when re-tested 14 days following infusion than animals similarly treated with HSV-LacZ (3d HSV-LacZ, n=3) or animals given HSV-CREB 14 days prior to massed training and tested 48 h later (14d HSV-CREB, n=4) ($F_{2,4}$=6.05, p<0.05).

The teachings of all the articles, patents and patent applications cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of identifying a gene or genes involved in transcription-dependent memory comprising the steps of:
   (a) training non-human animals under conditions sufficient to induce transcription-dependent memory formation in said non-human animals;
   (b) extracting RNA from brain tissue of said non-human animals trained in step (a);
   (c) synthesizing DNA probes using the RNA extracted in step (b);
   (d) exposing the DNA probes synthesized in step (c) to microarray chips containing DNA sequences from genes of the genome of said non-human animals under conditions appropriate for hybridization of the DNA probes to complementary DNA sequences on the microarray chips, wherein a signal is produced upon hybridization of said probes to complementary DNA sequences;
   (e) detecting the signal produced in step (d); and
   (f) performing a statistical comparison between the signal detected in step (e) and the signal detected in a control, wherein said control is obtained according to a method comprising the steps of:
   (i) training non-human control animals under appropriate conditions, wherein said conditions are insufficient to induce transcription-dependent memory formation in said non-human control animals;
   (ii) extracting RNA from brain tissue of said non-human control animals trained in step (f)(i);
   (iii) synthesizing DNA probes using the RNA extracted in step (f)(ii); and
   (iv) exposing the DNA probes synthesized in step (f)(iii) to microarray chips containing DNA sequences from genes of the genome of non-human control animals under conditions appropriate for hybridization of the DNA probes to complementary DNA sequences on the microarray chips, wherein a signal is produced upon hybridization of said probes to complementary DNA sequences.

2. The method of claim 1 wherein said non-human animals and said non-human control animals are non-human mammals.

3. The method of claim 1 wherein said transcription-dependent memory formation is long term memory formation.

4. The method of claim 1 wherein transcription-dependent memory formation is 10 induced using a spaced training protocol and the conditions of step (f)(i) are those according to a massed training protocol.

5. The method of claim 1 wherein the conditions of step (f)(i) are those sufficient to induce transcription-independent memory formation but not transcription-dependent memory formation.

6. The method of claim 5 wherein transcription-independent memory formation is induced using a massed training protocol.

7. The method of claim 1 wherein transcription-dependent memory formation is induced using a shuffle-box avoidance training protocol, the non-human control animals of step (f)(i) have a surgical lesion of the fornix and the conditions of step (f)(i) are those according to the shuttle-box avoidance training protocol.

8. The method of claim 7 wherein said non-human animals and said non-human control animals are non-human mammals.

9. The method of claim 1 wherein transcription-dependent memory formation is induced using a contextual fear conditioning training protocol, the non-human control animals of step (f)(i) are habituated to the training chamber before training and the conditions of step (f)(i) are those according to the contextual fear conditioning training protocol.

10. The method of claim 9 wherein said non-human animals and said non-human control animals are non-human mammals.

11. A method of identifying a gene or genes involved in transcription-dependent memory comprising the steps of:
   (a) training Drosophila under conditions appropriate to induce transcription-dependent memory formation in said Drosophila;
   (b) extracting RNA from head tissue of Drosophila trained in step (a);
   (c) synthesizing DNA probes using the RNA extracted in step (b);
   (d) exposing the DNA probes synthesized in step (c) to microarray chips containing DNA sequences from genes of the Drosophila genome under conditions appropriate for hybridization of the DNA probes to complementary DNA sequences on the microarray chips, wherein a signal is produced upon hybridization of said probes to complementary DNA sequences;
   (e) detecting the signal produced in step (d); and
   (f) performing a statistical comparison between the signal detected in step (e) and the signal detected in a control, wherein said control is obtained according to a method comprising the steps of:
   (i) training control Drosophila under appropriate conditions, wherein said conditions are insufficient to induce transcription-dependent memory formation in said control Drosophila;
   (ii) extracting RNA from head tissue of said control Drosophila trained in step (f)(i);
   (iii) synthesizing DNA probes using the RNA extracted in step (f)(ii); and
   (iv) exposing the DNA probes synthesized in step (f)(iii) to microarray chips containing DNA sequences from genes of the Drosophila genome under conditions appropriate for hybridization of the DNA probes to complementary DNA sequences on the microarray chips, wherein a signal is produced upon hybridization of said probes to complementary DNA sequences.

12. The method of claim 11 wherein said transcription-dependent memory formation is long term memory formation.

13. The method of claim 11 wherein transcription-dependent memory formation is induced using a spaced training protocol and the conditions of step (f)(i) are those according to a massed training protocol.

14. The method of claim 11 wherein the conditions of step (f)(i) are those sufficient to induce transcription-independent memory formation but not transcription-dependent memory formation.

15. The method of claim 14 wherein transcription-independent memory formation is induced using a massed training protocol.

16. A method of identifying a gene or genes involved in transcription-dependent memory comprising the steps of:
  (a) training non-human animals under conditions sufficient to induce transcription-dependent memory formation in said non-human animals;
  (b) extracting RNA from brain tissue of said non-human animals trained in step (a);
  (c) synthesizing DNA probes using the RNA extracted in step (b);
  (d) exposing the DNA probes synthesized in step (c) to microarray chips containing DNA sequences from genes of the genome of said non-human animals under conditions appropriate for hybridization of the DNA probes to complementary DNA sequences on the microarray chips, wherein a signal is produced upon hybridization of said probes to complementary DNA sequences;
  (e) amplifying a signal from hybridized probes;
  (f) detecting the signal produced in step (e); and
  (g) performing a statistical comparison between the signal detected in step (e) (f) and the signal detected in a control, wherein said control is obtained according to a method comprising the steps of:
    (i) extracting RNA from brain tissue of non-human control animals;
    (ii) synthesizing DNA probes using the RNA extracted in step (g)(i); and
    (iii) exposing the DNA probes synthesized in step (g)(ii) to microarray chips containing DNA sequences from genes of the genome of non-human control animals under conditions appropriate for hybridization of the DNA probes to complementary DNA sequences on the microarray chips, wherein a signal is produced upon hybridization of said probes to complementary DNA sequences.

17. The method of claim 16 wherein said non-human animals and said non-human control animals are non-human mammals.

18. The method of claim 16 wherein said transcription-dependent memory formation is long term memory formation.

19. The method of claim 16 wherein transcription-dependent memory formation is induced using a spaced training protocol.

20. The method of claim 16 wherein transcription-dependent memory formation is induced using a shuttle-box avoidance training protocol.

21. The method of claim 20 wherein said non-human animals and said non-human control animals are non-human mammals.

22. The method of claim 16 wherein transcription-dependent memory formation is induced using a contextual fear conditioning training protocol.

23. The method of claim 22 wherein said non-human animals and said non-human control animals are non-human mammals.

24. A method of identifying a gene or genes involved in transcription-dependent memory comprising the steps of:
  (a) training *Drosophila* under conditions appropriate to induce transcription-dependent memory formation in said *Drosophila*;
  (b) extracting RNA from head tissue of *Drosophila* trained in step (a);
  (c) synthesizing DNA probes using the RNA extracted in step (b);
  (d) exposing the DNA probes synthesized in step (c) to microarray chips containing DNA sequences from genes of the *Drosophila* genome under conditions appropriate for hybridization of the DNA probes to complementary DNA sequences on the microarray chips, wherein a signal is produced upon hybridization of said probes to complementary DNA sequences;
  (e) amplifying a signal from hybridized probes;
  (f) detecting the signal produced in step (e); and
  (g) performing a statistical comparison between the signal detected in step (f) and the signal detected in a control, wherein said control is obtained according to a method comprising the steps of:
    (i) extracting RNA from head tissue of control *Drosophila*;
    (ii) synthesizing DNA probes using the RNA extracted in step (g)(i); and
    (iii) exposing the DNA probes synthesized in step (g)(ii) to microarray chips containing DNA sequences from genes of the *Drosophila* genome under conditions appropriate for hybridization of the DNA probes to complementary DNA sequences on the microarray chips, wherein a signal is produced upon hybridization of said probes to complementary DNA sequences.

25. The method of claim 24 wherein said transcription-dependent memory formation is long term memory formation.

26. The method of claim 24 wherein transcription-dependent memory formation is induced using a spaced training protocol.

* * * * *

UNITED STATES PATENT AND TRADEMARK OFFICE
CERTIFICATE OF CORRECTION

PATENT NO. : 7,358,049 B2  Page 1 of 1
APPLICATION NO. : 11/199563
DATED : April 15, 2008
INVENTOR(S) : Timothy P. Tully et al.

It is certified that error appears in the above-identified patent and that said Letters Patent is hereby corrected as shown below:

Claim 4, line 2, delete "10"

Claim 7, line 2, change "shuffle-box" to --shuttle-box--; and
    line 5, delete "20"

Claim 16, line 21, delete "(e)".

Signed and Sealed this

Eleventh Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,358,049 B2  
APPLICATION NO. : 11/199563  
DATED : April 15, 2008  
INVENTOR(S) : Timothy P. Tully et al.

Page 1 of 1

It is certified that error appears in the above-identified patent and that said Letters Patent is hereby corrected as shown below:

Column 25, Claim 4, line 61, delete "10"

Column 26, Claim 7, line 18, change "shuffle-box" to --shuttle-box--; and
line 21, delete "20"

Column 27, Claim 16, line 39, delete "(e)".

This certificate supersedes the Certificate of Correction issued August 11, 2009.

Signed and Sealed this

First Day of September, 2009

David J. Kappos
*Director of the United States Patent and Trademark Office*